United States Patent
Saito

(10) Patent No.: US 7,434,998 B2
(45) Date of Patent: Oct. 14, 2008

(54) X-RAY CT SCANNER WITH GRAPHICAL SETTING OF BEAM THICKNESS

(75) Inventor: Yasuo Saito, Nasu-gun (JP)

(73) Assignee: Kabushiki Kaisha Toshiba, Tokyo (JP)

(*) Notice: Subject to any disclaimer, the term of this patent is extended or adjusted under 35 U.S.C. 154(b) by 0 days.

(21) Appl. No.: 11/211,655

(22) Filed: Aug. 26, 2005

(65) Prior Publication Data

US 2006/0002505 A1 Jan. 5, 2006

Related U.S. Application Data

(60) Continuation of application No. 10/413,210, filed on Apr. 15, 2003, now abandoned, which is a division of application No. 09/983,324, filed on Oct. 24, 2001, now Pat. No. 6,568,851.

(30) Foreign Application Priority Data

Oct. 25, 2000 (JP) .............................. 2000-325920

(51) Int. Cl.
*G01D 18/00* (2006.01)
*G21K 1/04* (2006.01)

(52) U.S. Cl. ...................... 378/207; 378/150
(58) Field of Classification Search ............... 378/4, 378/19, 147, 150, 151, 152, 16, 207
See application file for complete search history.

(56) References Cited

U.S. PATENT DOCUMENTS

| | | | |
|---|---|---|---|
| 4,787,098 A | 11/1988 | Silver | 378/18 |
| 5,117,446 A * | 5/1992 | Haaker et al. | 378/98.3 |
| 5,241,576 A | 8/1993 | Lonn | 378/19 |
| 5,377,252 A * | 12/1994 | Liebetruth | 378/151 |
| 5,568,530 A | 10/1996 | Saito et al. | 378/4 |
| 5,864,597 A * | 1/1999 | Kobayashi | 378/4 |
| 5,982,846 A * | 11/1999 | Toth et al. | 378/19 |

(Continued)

FOREIGN PATENT DOCUMENTS

JP 09-122112 5/1997

(Continued)

OTHER PUBLICATIONS

U.S. Appl. No. 11/211,655, filed Aug. 26, 2005, Saito.

*Primary Examiner*—Allen C. Ho
(74) *Attorney, Agent, or Firm*—Oblon, Spivak, McClelland, Maier & Neustadt, P.C.

(57) ABSTRACT

An X-ray CT scanner includes an X-ray tube which irradiates an object, a variable X-ray limiting device which limits the X-ray beam thickness, an X-ray detector which detects X rays transmitted through the object and has a plurality of detecting elements arrayed in a matrix manner, a storing unit which stores a plurality of calibration data files corresponding to a plurality of beam thicknesses, a correcting unit which corrects an output from the X-ray detector on the basis of at least one calibration data file read out from the storing unit, a reconstructing unit which reconstructs image data concerning the object on the basis of an output from the correcting unit, and a control unit which controls the variable X-ray limiting device to change the beam thickness of the X rays, independently of the beam thicknesses to which the calibration data files stored correspond.

8 Claims, 20 Drawing Sheets

U.S. PATENT DOCUMENTS

| | | | |
|---|---|---|---|
| 6,061,420 A | 5/2000 | Strong et al. ................... 378/4 |
| 6,157,696 A | 12/2000 | Saito et al. ................... 378/19 |
| 6,173,039 B1 | 1/2001 | Hampel et al. ............. 378/150 |
| 6,178,228 B1 * | 1/2001 | Schol ......................... 378/162 |
| 6,198,791 B1 * | 3/2001 | He et al. ....................... 378/19 |
| 6,215,844 B1 | 4/2001 | Adachi et al. ................ 378/19 |
| 6,222,544 B1 * | 4/2001 | Tarr et al. ................... 715/839 |
| 6,243,438 B1 | 6/2001 | Nahaliel et al. .............. 378/19 |
| 6,298,117 B1 | 10/2001 | Hampel et al. ............. 378/150 |
| 6,359,956 B1 * | 3/2002 | Hsieh et al. ................... 378/15 |
| 6,363,134 B1 * | 3/2002 | Suzuki ......................... 378/15 |
| 6,396,898 B1 | 5/2002 | Saito et al. ................... 378/19 |
| 6,404,841 B1 * | 6/2002 | Pforr et al. .................... 378/4 |
| 6,404,844 B1 * | 6/2002 | Horiuchi et al. ............... 378/8 |
| 6,445,764 B2 | 9/2002 | Gohno et al. ................ 378/19 |
| 6,449,340 B1 | 9/2002 | Tybinkowski et al. ....... 378/150 |
| 6,463,121 B1 * | 10/2002 | Milnes ......................... 378/62 |
| 6,501,827 B1 * | 12/2002 | Takasawa ................... 378/62 |
| 6,512,808 B2 | 1/2003 | Klingenbeck-Regn ....... 378/18 |
| 6,568,851 B2 * | 5/2003 | Saito ......................... 378/207 |
| 6,587,538 B2 | 7/2003 | Igarashi et al. ................ 378/19 |
| 6,619,839 B2 * | 9/2003 | Yoshimura ................. 378/196 |
| 6,650,727 B2 * | 11/2003 | Kuroda ........................ 378/19 |
| 6,677,962 B1 * | 1/2004 | Bailey ........................ 715/744 |
| 6,795,526 B2 * | 9/2004 | Kump et al. ................ 378/116 |
| 6,944,269 B2 * | 9/2005 | Schmitt ...................... 378/115 |
| 6,990,170 B2 * | 1/2006 | Sugihara et al. ............... 378/15 |
| 7,031,423 B2 * | 4/2006 | Tsukagoshi .................... 378/4 |
| 7,054,406 B2 * | 5/2006 | Ikeda et al. .................... 378/8 |
| 7,162,064 B2 * | 1/2007 | Klingenbeck-Regn ...... 382/131 |
| 7,215,733 B2 * | 5/2007 | Nabatame .................... 378/16 |
| 7,334,940 B2 * | 2/2008 | Nukui ......................... 378/207 |

FOREIGN PATENT DOCUMENTS

| | | |
|---|---|---|
| JP | 10-024031 | 1/1998 |
| JP | 10-033520 | 2/1998 |
| JP | 10-314152 | 12/1998 |
| JP | 2000-070254 | 3/2000 |
| JP | 2000-139894 | 5/2000 |
| JP | 2000-166911 | 6/2000 |

* cited by examiner

X-RAY CT SCANNER WITH GRAPHICAL SETTING OF BEAM THICKNESS

CROSS-REFERENCE TO RELATED APPLICATIONS

This application is a continuation application of U.S. Ser. No. 10/413,210, filed Apr. 15, 2003, which is a divisional of U.S. Ser. No. 09/983,324, filed on Oct. 24, 2001, now U.S. Pat. No. 6,568,851 and is based upon and claims the benefit of priority from the prior Japanese Patent Application No. 2000-325920, filed Oct. 25, 2000, the entire contents of which are incorporated herein by reference.

BACKGROUND OF THE INVENTION

1. Field of the Invention

The present invention relates to an X-ray CT scanner having a correcting function.

2. Description of the Related Art

An X-ray CT scanner is an apparatus which generates tomogram data by reconstructing, by using a computer, projection data obtained by irradiating an object to be examined with X-rays from the circumference of the object. These X-ray CT scanners are classified into the following three types in accordance with differences between the forms of X-ray beams.

The first one is a "fan-beam X-ray CT scanner" which radiates a fan-shaped X-ray beam from an X-ray tube. This fan-beam X-ray CT scanner acquires projection data by using an X-ray detector obtained by arranging about, e.g., 1,000 channels of detecting elements in a line. Projection data acquiring operation is repeated about 1,000 times while the X-ray tube rotates around an object to be examined. This fan-beam X-ray CT scanner is also called a "single-slice CT scanner" because data concerning a single slice are acquired.

The second one is a so-called "multi-slice X-ray CT scanner" in which several X-ray detectors each obtained by arranging about 1,000 channels of detecting elements in a line are juxtaposed in a slice direction. A slightly thick X-ray beam is radiated in accordance with the width of these juxtaposed detectors. This multi-slice X-ray CT scanner is so called because data of several slices can be simultaneously acquired.

The third one is a so-called "cone-beam X-ray CT scanner" in which a plurality of detecting elements each composed of a combination of, e.g., a scintillator and a photodiode are two-dimensionally arrayed. A conical or pyramidal X-ray beam is radiated in accordance with the width of these detecting elements in a slice direction. This cone-beam X-ray CT scanner is also called a volume X-ray CT scanner because volume data can be acquired at once.

The research of a cone-beam X-ray CT scanner has been advanced primarily on a system using an image intensifier (I.I.) as an X-ray detector since late 1980s. For example, in "Volume CT of anthropomorphic using a radiation therapy simulator" (Michael D. Silver, Yasuo Saito et al.; SPIE 1651 197-211 (1992)), the results of scan of chest phantoms in an experimental system combining a turntable and an I.I. are discussed. Some cone-beam X-ray CT scanners are beginning to be put into practical use as apparatuses for obtaining the shapes of high-contrast objects such as bones and blood vessels in angiography.

As described above, a cone-beam X-ray CT scanner has a wider divergent angle of an X-ray beam in a slice direction than in the other two types. In other words, the X-ray beam is thick on the rotation central axis. Since this increases the number of paths through which scattered rays reach detecting elements, the scattered ray amount increases. Scattered rays cause abuses, e.g., deteriorate the image contrast. This scattered ray increasing mechanism means that the scattered ray amount varies in accordance with a change in the beam thickness.

An X-ray CT scanner usually performs sensitivity correction in order to equalize the sensitivities of detecting elements. For this purpose, calibration data files (calibration data) for sensitivity correction are acquired by using a phantom (pseudo model). Since scattered rays change in accordance with the beam thickness as described above, these calibration data files must also be selectively used in accordance with the beam thickness.

This paradoxically means that the degree of freedom of beam thickness adjustment is limited by the types of calibration data files that the apparatus has.

Assume, for example, that a calibration data file acquired by a beam thickness $X1$ and a calibration data file acquired by a beam thickness $X2$ ($>X1$) are prepared. In this case, no corresponding calibration data files are prepared for beam thicknesses other than $X1$ and $X2$. Therefore, no such beam thicknesses can be set except when the inclusion of a scattered ray error is permitted.

BRIEF SUMMARY OF THE INVENTION

It is an object of the present invention to provide an X-ray CT scanner capable of extending the degree of freedom of setting of an X-ray beam thickness.

According to a certain aspect of the present invention, an X-ray CT scanner comprises an X-ray tube which irradiates an object to be examined with X rays, a variable X-ray limiting device which limits the beam thickness of the X rays, an X-ray detector which detects X rays transmitted through the object and has a plurality of detecting elements arrayed in a matrix manner, a storing unit which stores a plurality of calibration data files corresponding to a plurality of beam thicknesses, a correcting unit which corrects an output from the X-ray detector on the basis of at least one calibration data file read out from the storing unit, a reconstructing unit which reconstructs image data concerning the object on the basis of an output from the correcting unit, and a control unit which controls the variable X-ray limiting device to change the beam thickness of the X rays, independently of the plurality of beam thicknesses to which the plurality of calibration data files stored correspond.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention and, together with the generation description given above and the detailed description of the embodiments given below, serve to explain the principles of the invention.

DETAILED DESCRIPTION OF THE INVENTION

An embodiment of the present invention will be described below with reference the accompanying drawing.

Figure 1:
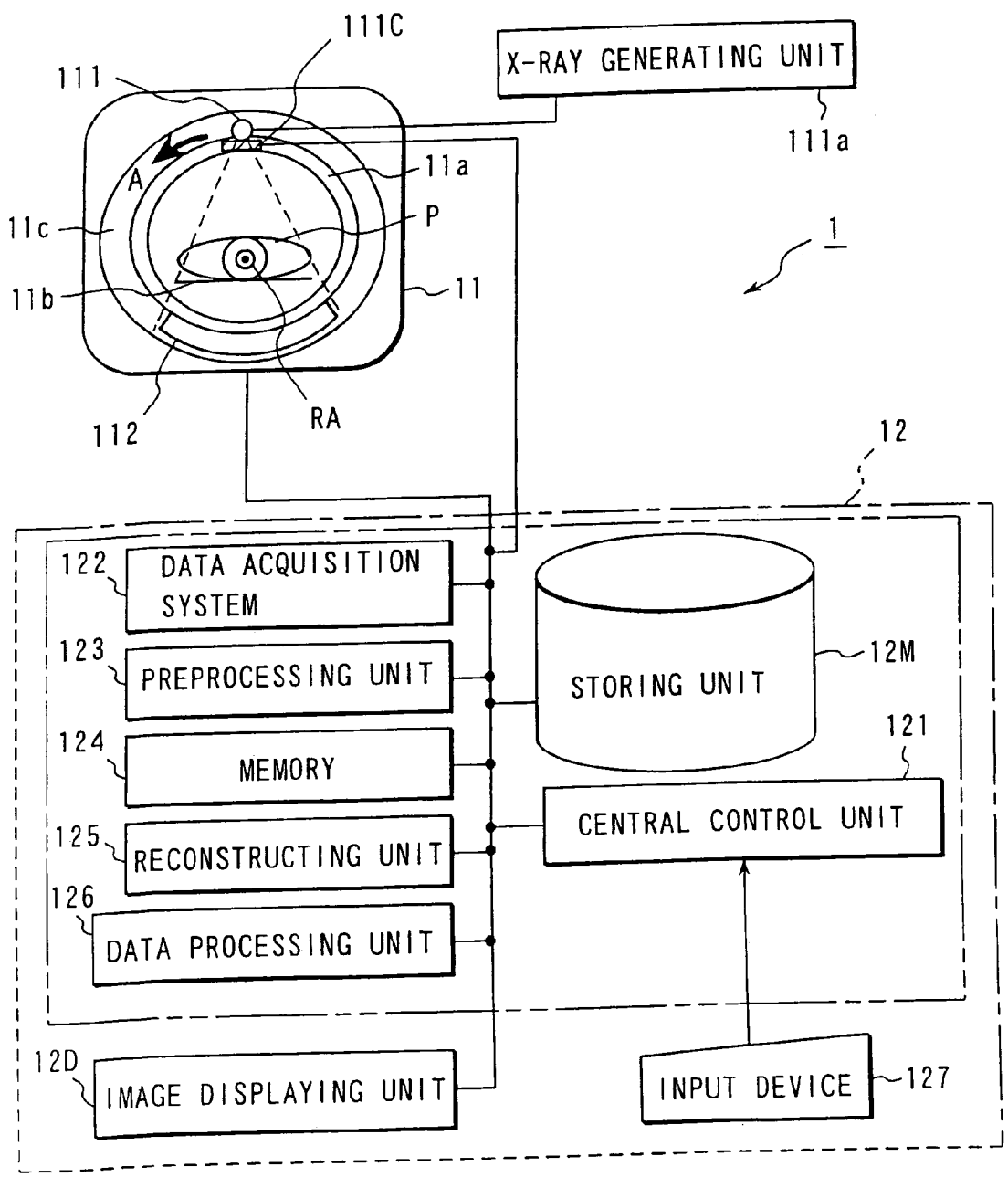
FIG. 1 is a schematic view showing the arrangement of an X-ray CT scanner according to an embodiment.

FIG. 1 is a schematic view showing the arrangement of an X-ray CT scanner according to this embodiment. Referring to FIG. 1, an X-ray CT scanner 1 includes a frame 11 and a console 12. The frame 11 has a hollow portion 11a. Into this hollow portion 11a, a patient P placed on a table top 11b of a bed is inserted. An X-ray tube 111 and an X-ray detector 112 are arranged around the hollow portion 11a. The X-ray tube 111 and the X-ray detector 112 are mounted to oppose each other on a rotary ring 11c held to be rotatable around a rotation central axis RA perpendicular to the drawing surface. The X-ray tube 111 is connected to an X-ray generating unit 111a including a high-voltage power supply. The X-ray detector 112 includes a plurality of detecting elements each composed of, e.g., a scintillator and a photodiode. These detecting elements are arrayed in a matrix manner in two directions, i.e., a direction parallel to the rotation central axis RA, and a direction substantially perpendicular to the rotation central axis RA. Note that the direction parallel to the rotation central axis RA will be referred to as a "slice direction" hereinafter, and the direction substantially perpendicular to the rotation central axis RA will be referred to as a "channel direction" hereinafter.

X-rays generated by the X-ray tube 111 irradiate the patient P as indicated by the broken lines in FIG. 1. X-rays transmitted through the patient P are converted into electric signals by the detecting elements of the X-ray detector 112 and acquired by a data acquisition system 122.

A variable X-ray limiting device (also called a collimator) 111c is attached to an X-ray emission window of the X-ray tube 111. This variable X-ray limiting device 111c has a plurality of shielding plates to limit the beam thickness of X-rays generated from the X-ray tube 111 in the slice direction. These shielding plates are so supported as to be individually movable in the slice direction. The X-ray beam thickness can be varied by adjusting the spacings between these shielding plates. The collimator 111c is typically a multi-leaf collimator. This multi-leaf collimator has a plurality of plate-like leaves constructing two leaf pairs. The multi-leaf collimator can freely limit the beam thickness of X-rays by moving these plate-like leaves independently of each other, such that the leaves come close to or move away from each other in the longitudinal direction.

The console 12 includes, e.g., a central control unit 121, an input device 127, and an image displaying unit 12D. The central control unit 121 controls the frame 11, the bed, the table top, and the like. The input device 127 is used by an operator to access this central control unit 121. The image displaying unit 12D displays reconstructed CT images (e.g., an axial image, multi-planar reconstruction image (MPR image), body surface image, and maximum intensity projection image (MIP image)). Of these devices, the input device 127 can be a pointing device such as a mouse or a track ball, and the image displaying unit 12D can be a CRT or the like.

An operator inputs a command to the central control unit 121 via the input device 127. In accordance with this input command, the central control unit 121 reconstructs tomogram data on the basis of an output from the X-ray detector 112, and displays the data on the image displaying unit 12D. More specifically, the tomogram or the like is reconstructed by the flow of data, or processing, conceptually shown in FIG. 2, in the data acquisition system 122, a preprocessing unit 123, a memory 124, a reconstructing unit 125, and a data processing unit 126 shown in FIG. 1. The reconstructed image is displayed on the image displaying unit 12D.

Figure 2:
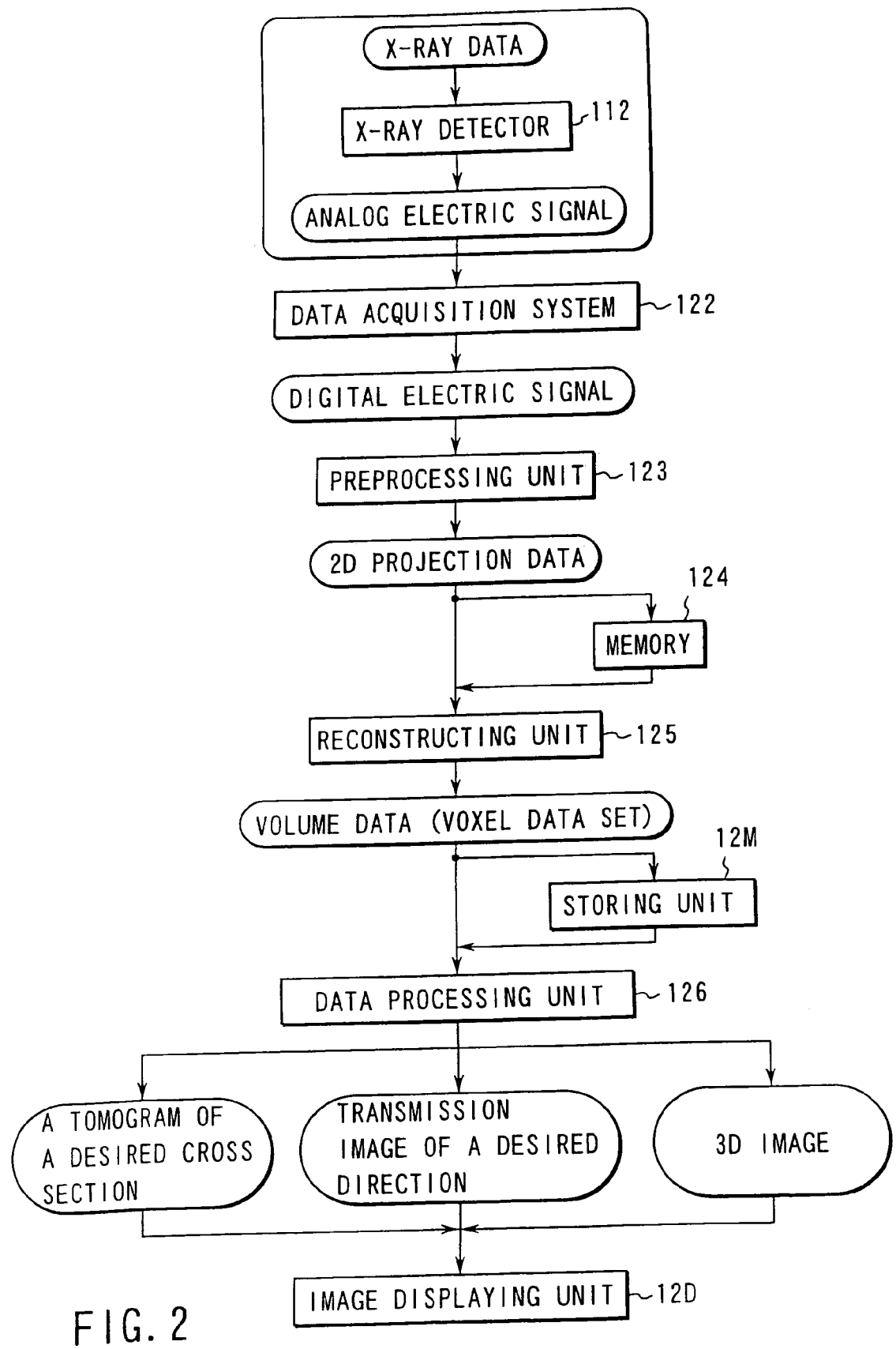
FIG. 2 is a view conceptually showing the flow of data in the X-ray CT scanner shown in FIG. 1.

Referring to FIG. 2, the data acquisition system 122 receives a plurality of electric signals from a plurality of detecting elements of the X-ray detector 112. This data acquisition system 122 amplifies these electric signals and outputs the amplified electric signals as digital signals via an A/D converter. A digital signal before being subjected to preprocessing is called raw data.

The preprocessing unit 123 corrects the raw data from the data acquisition system 122 on the basis of at least one calibration data file read out from a plurality of calibration data files stored in a storing unit 12M. This correction process includes, e.g., reference correction, water correction, and sensitivity correction. The data corrected by this preprocessing unit 123 is data immediately before reconstruction and is called "projection data".

The memory 124 stores this projection data. The reconstructing unit 125 receives the projection data from the memory 124. On the basis of this projection data, the reconstructing unit 125 reconstructs the distribution (called volume data or voxel data) of X-ray absorption coefficients in a three-dimensional region extending in the slice direction of the patient P, by using a three-dimensional image reconstructing algorithm represented by, e.g., a method called a Feldkamp method. In the above description, the projection data is once stored in the storing unit 124. In some cases, however, the projection data can be directly supplied from the preprocessing unit 123 to the reconstructing unit 125 without being stored in the memory 124.

The volume data is supplied to the data processing unit 126 directly or after being once stored in the storing unit 12M. From this volume data, the data processing unit 126 generates image data for display, such as a tomogram of a desired cross section, a transmission image of a desired direction, or a so-called three-dimensional image capable of two-dimensionally expressing a stereoscopic structure. The image displaying unit 12D displays this image data for display in gray scale or in color. The image data for display and the volume data are stored in the storing unit 12M typically implemented by a hard disk drive.

Note that the arrangement of the X-ray CT scanner 1 shown in FIG. 1 is merely an example. That is, in FIG. 1 the reconstructing unit 125 and the like are configured as the console 12 separately from the frame 11. However, the reconstructing unit 125 and the like can also be installed in the frame 11. It is also possible to install the data acquisition unit 122 in the frame 11, and the preprocessing unit 123 and subsequent units in the console 12. In this case, the transmission of electric signals from the former to the latter is performed using a non-contact data transmitting means (not shown).

A sensitivity correction process by the preprocessing unit 123 will be described below with reference to flow charts shown in FIGS. 3 and 9.

Figure 3:
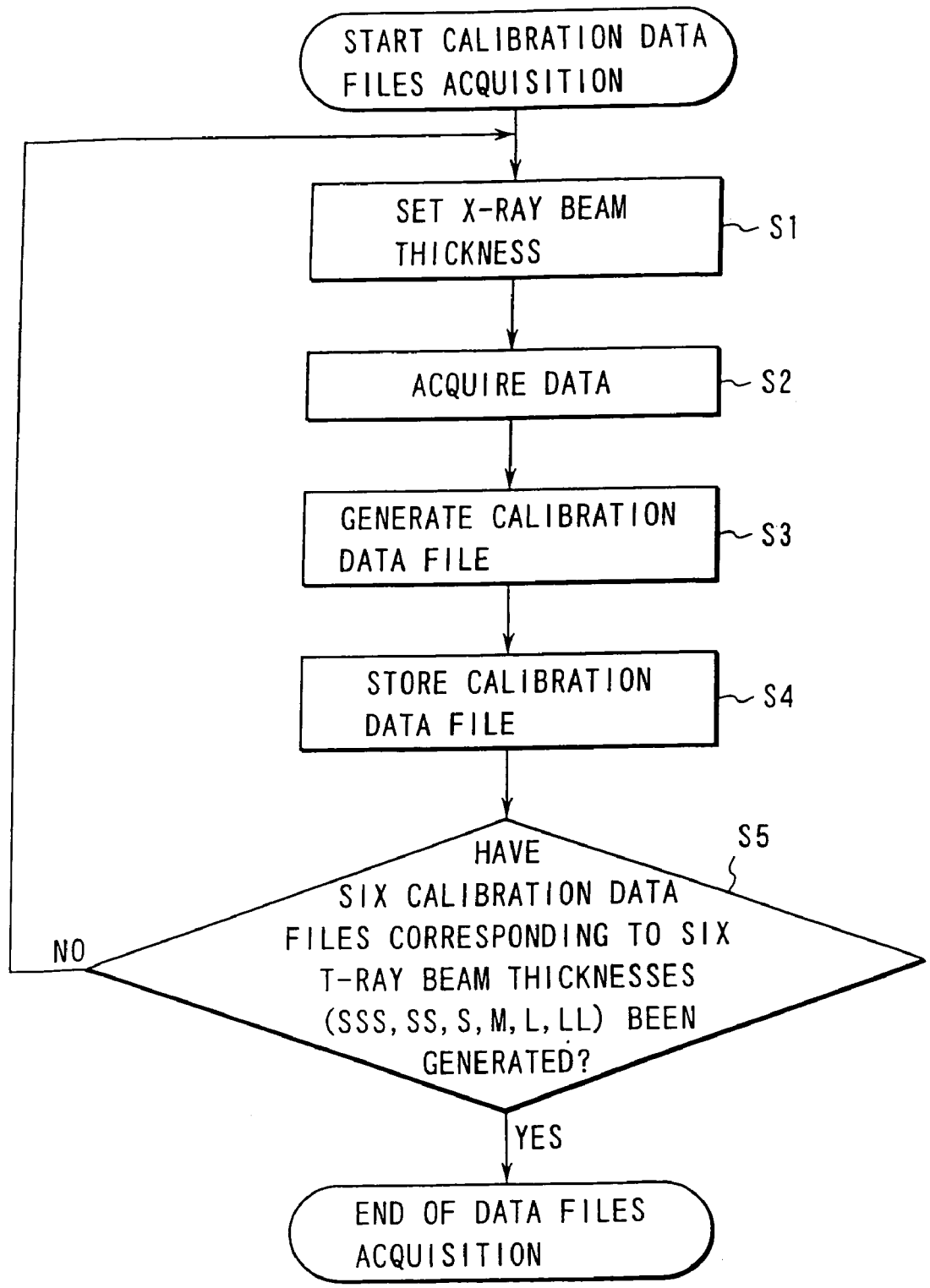
FIG. 3 is a flow chart showing the flow of a calibration data file acquisition process in the X-ray CT scanner shown in FIG. 1.

FIG. 3 shows a calibration data file acquisition process. Raw data is corrected on the basis of a calibration data file. This correction is the process of equalizing the sensitivities of the detecting elements of the X-ray detector 112. By this correction, the CT value of water and the CT value of air are standardized to "0" and "−1,000", respectively. A calibration data file is generated from data acquired under the same "scan conditions" as actual examination by using a cylindrical model filled with water, i.e., a "water phantom". The "scan conditions" include a field of view (FOV), an approximate diameter of the patient P, a tube voltage, a tube current, and the like.

The field of view FOV is a region as an object of reconstruction, and is formed into a columnar shape around the rotation central axis RA. The size of this field of view FOV is defined by its radius and length. Generally, the beam thickness of X-rays is so determined that the X-rays cover the entire field of view FOV. The X-ray beam thickness is defined as the thickness of an X-ray bundle on the rotation central axis RA. This X-ray beam thickness is determined by the size of the field of view FOV. Conversely, when the X-ray beam thickness is determined, the size of the field of view FOV is determined accordingly. That is, the X-ray beam thickness and the size of the field of view FOV are parameters which define each other. In the following explanation, the term "X-ray beam thickness" is used, but this term can also be reread as the size of the field of view FOV.

In step S1 of FIG. 3, a phantom is placed between the X-ray tube 111 and the X-ray detector 112, and this phantom is irradiated with X-rays limited to a specific beam thickness through the collimator 111c. In step S2, the X-rays transmitted through the phantom are detected by the detector 112, and data (phantom data files) are acquired. This phantom data file acquisition is repeated every predetermined cycle while the X-ray tube 111 rotates around the phantom. Consequently, a plurality of phantom data files are acquired in one-to-one correspondence with a plurality of points discretely arranged at fixed intervals on the rotational orbit along which the X-ray tube 111 rotates around the phantom.

In step S3, the data processing unit 126 calculates a calibration data file from the acquired phantom data files. The method of this calculation can be an arbitrary one. For example, the average addition value is calculated for each channel from the acquired phantom data files. A set of these average addition values is a calibration data file. Noise can be reduced by this addition average.

In step S4, the calibration data file thus calculated is stored in the storing unit 12M.

The routine from S1 to S4 is repeated until a plurality of calibration data files are acquired in one-to-one correspondence with a plurality of predetermined beam thicknesses (step S5).

Figure 4:
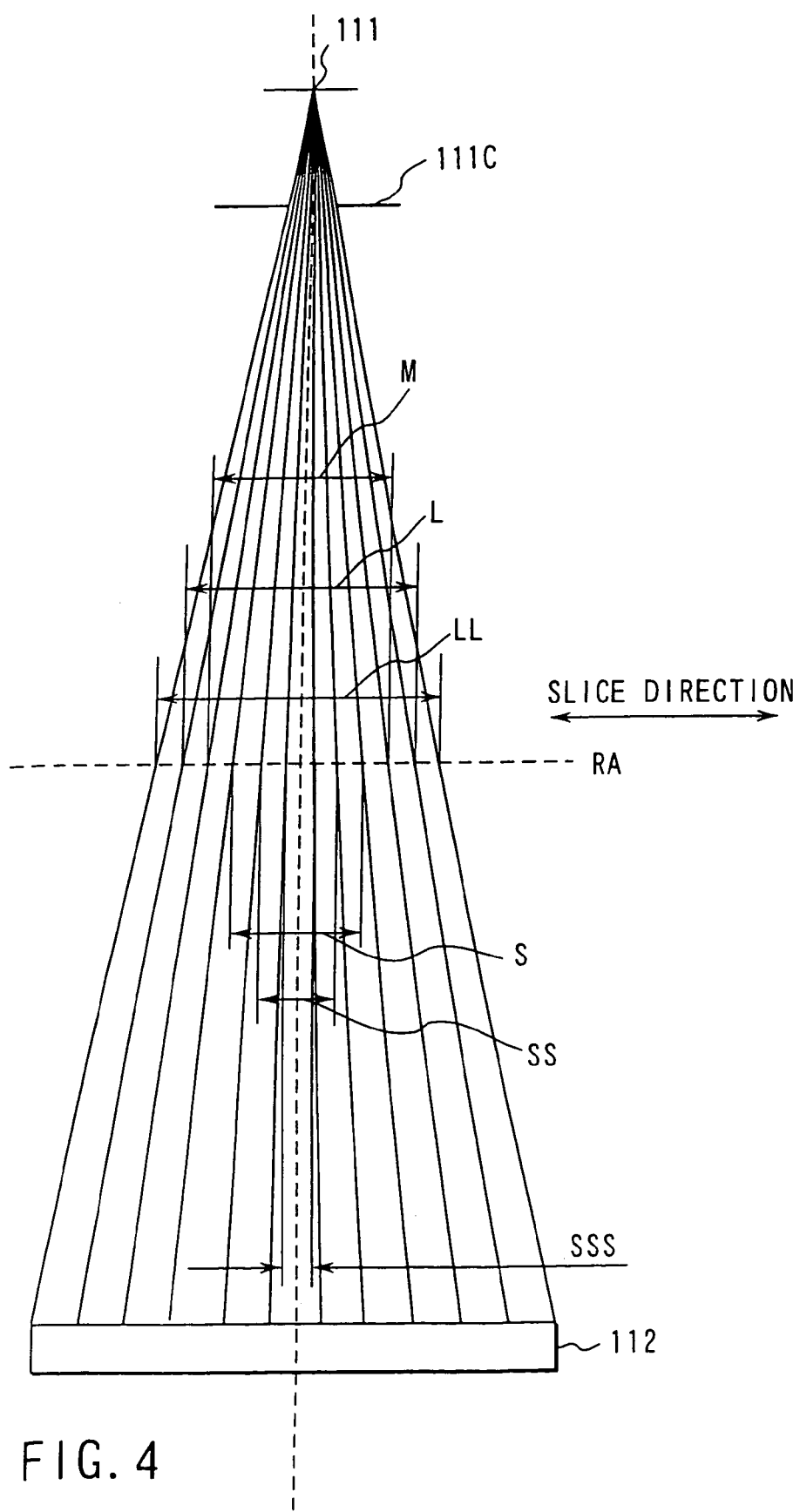
FIG. 4 is a view showing six different beam thicknesses to which a plurality of calibration data files stored in a storing unit shown in FIG. 1 correspond.
Figure 5:
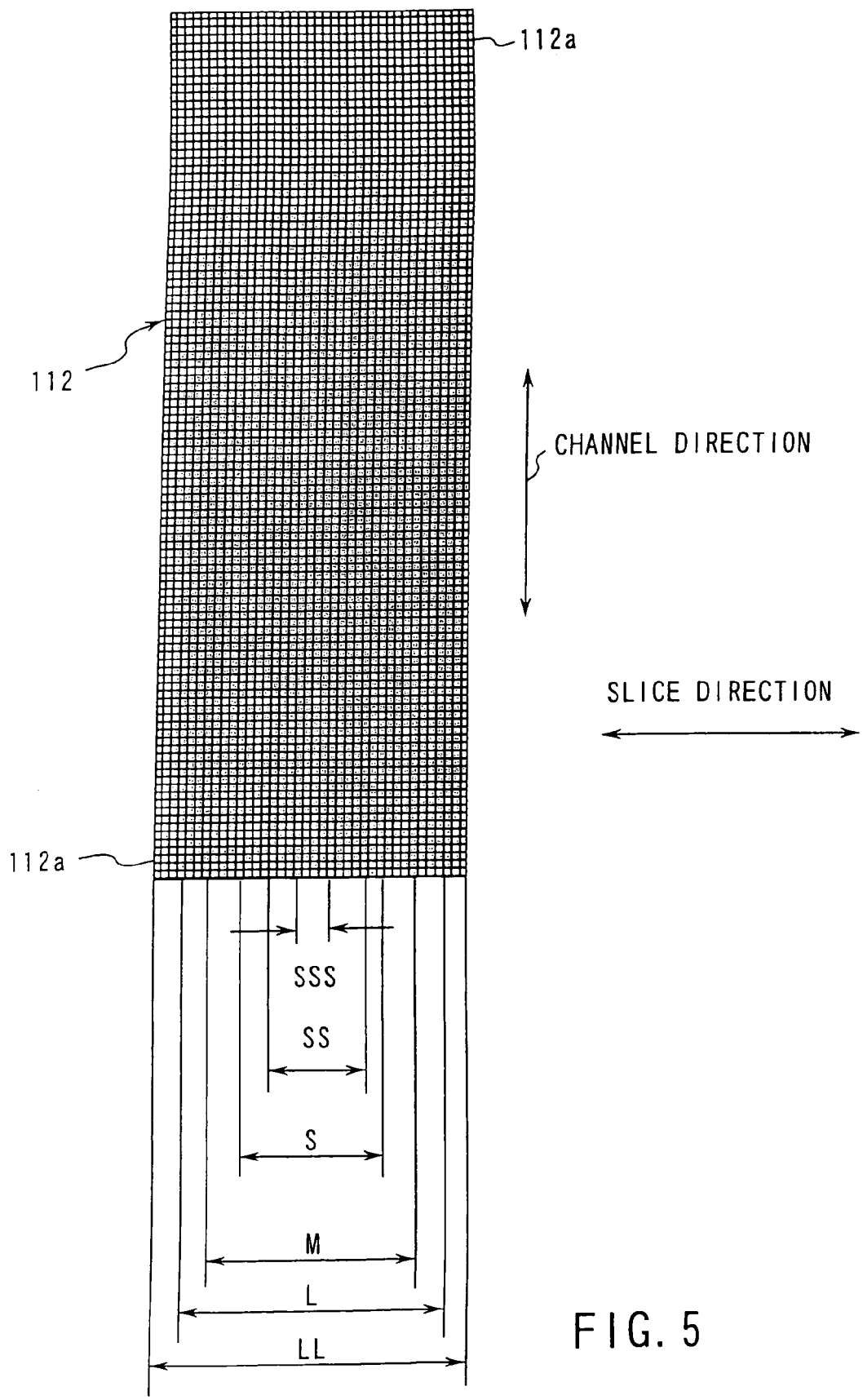
FIG. 5 is a view showing the relationship between the six different beam thicknesses shown in FIG. 4 and an X-ray detector.

FIG. 4 shows examples of a plurality of beam thicknesses previously determined to acquire a plurality of calibration data files. FIG. 5 is a plan view showing the X-ray detector 112 viewed from a point at which the X-ray tube 111 exists. FIG. 5 shows the relationship between the range of the X-ray detector 112 within which effective data is detected, i.e., the use region of the X-ray detector 112, and the beam thicknesses shown in FIG. 4.

As shown in FIGS. 4 and 5, in the slice direction of the patient P, a total of six different beam thicknesses, i.e., a maximum beam thickness "LL" determined by the use region of the X-ray detector 112, and subsequent beam thicknesses "L", "M", "S", "SS", and "SSS", are set at substantially equal spacings. That is, six calibration data files are acquired in one-to-one correspondence with these six different beam thicknesses.

The X-ray detector 112 has a plurality of detecting elements 112a arranged in an m×n matrix manner in the two, slice and channel directions. A center-to-center distance between the detecting elements 112a adjacent in the channel direction is, e.g., 1 mm, the distance is defined as the distance on the rotation central axis RA. A center-to-center distance between the detecting elements 112a adjacent in the slice direction is designed to be 1 mm, the same value, the distance is defined as the distance on the rotation central axis RA.

The maximum beam thickness LL is given by n×1 mm. In actual scanning, the beam thickness can be finely set in units of 1 mm from 1 mm to n×1 mm. Six different calibration data files are acquired for beam thicknesses, in this embodiment the six different, discrete beam thicknesses, fewer than the settable beam thicknesses. It is of course also possible to acquire calibration data files for all the settable beam thicknesses, but this is not practical. As is well known, the sensitivity of the detecting element 112a varies with time. Accordingly, calibration data files must be updated whenever the main power supply is turned on, or periodically. If the calibration data file acquiring operation is repeated for all the beam thicknesses whenever update is executed, the time of this updating operation is significantly increased.

Figure 6:
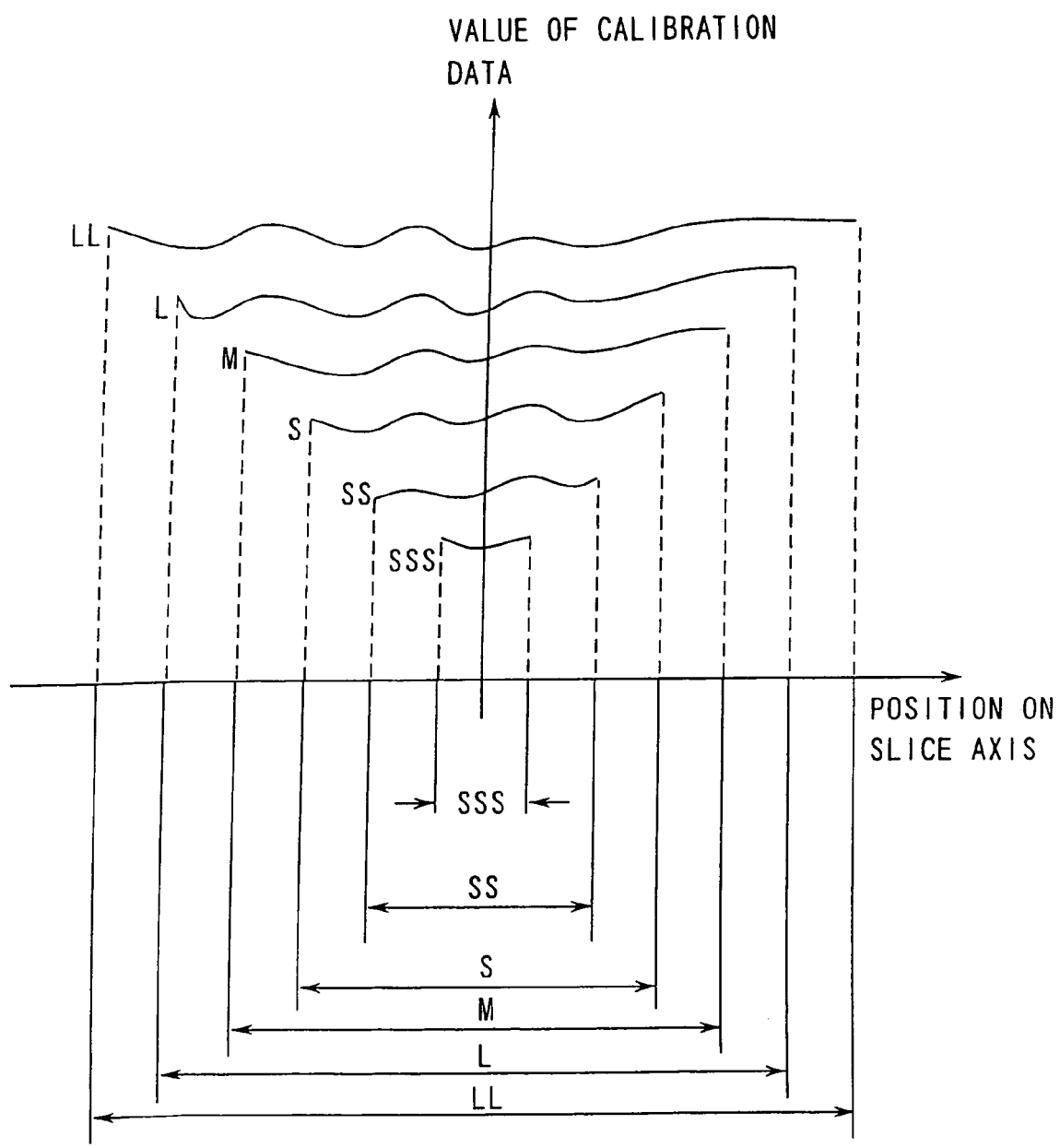
FIG. 6 is a view showing six calibration data files corresponding to the six different beam thicknesses shown in FIG. 4.
Figure 7A:
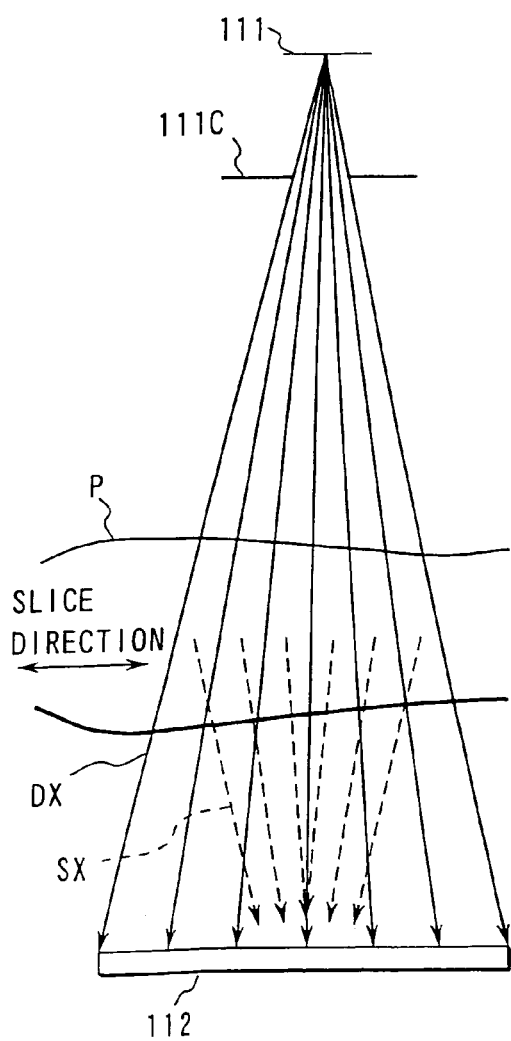
FIGS. 7A and 7B are views showing the relationship between the beam thickness and the scattered ray amount in this embodiment.
Figure 7B:
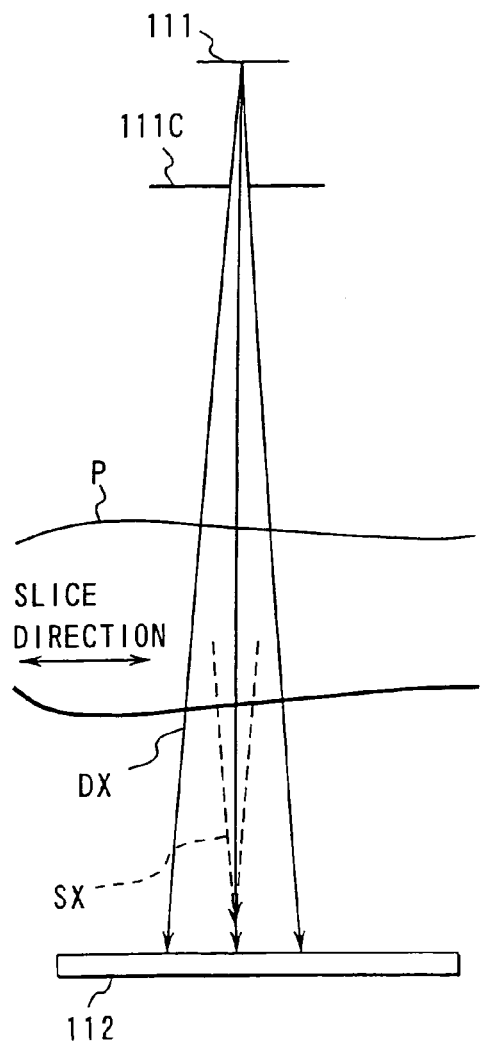
Figures 8A, 8B:
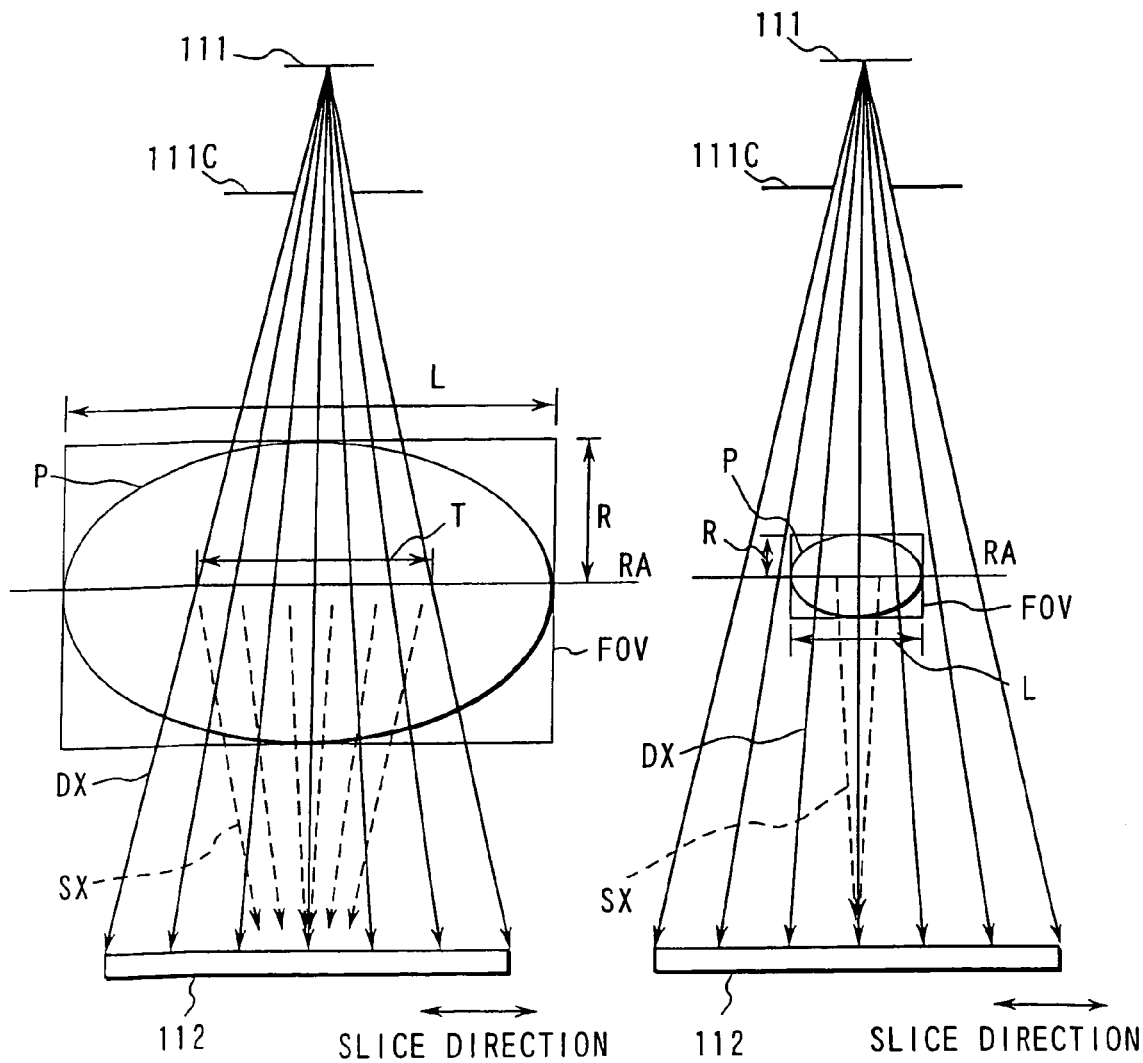
FIGS. 8A and 8B are views showing the relationship between the size of an object to be examined and the scattered ray amount.
Figure 19:
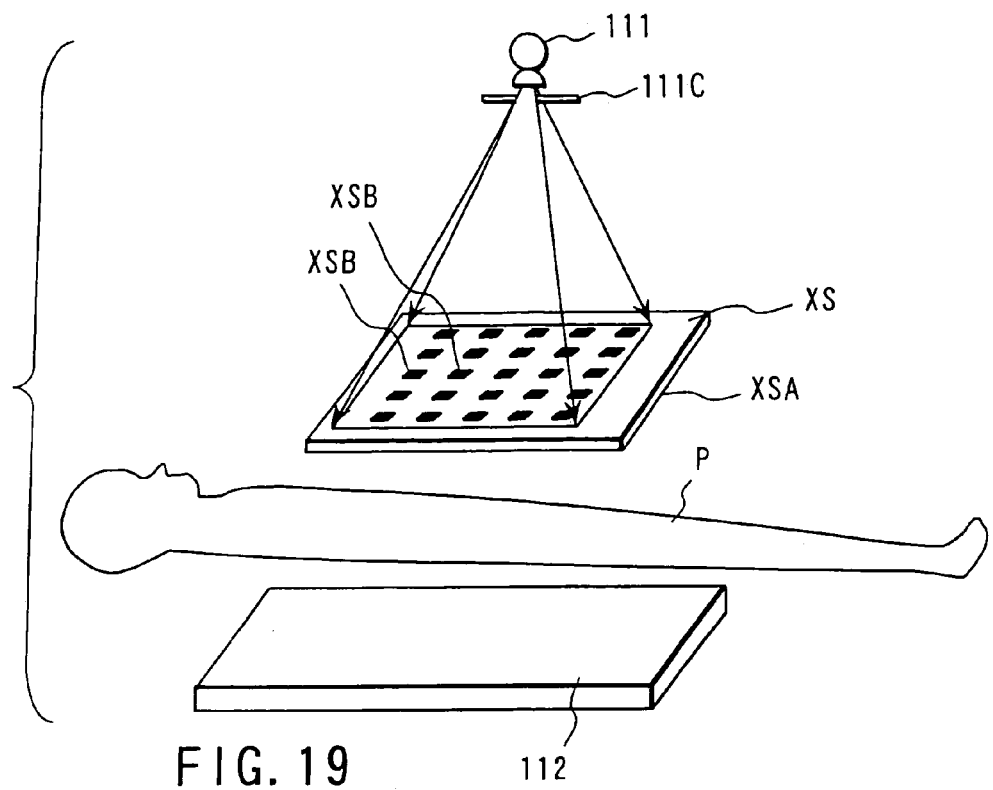
FIG. 19 is a view showing a system configuration for practicing a scattered ray correction process, disclosed in Jpn. Pat. No. 1631264.

FIG. 6 shows the six different calibration data files obtained for the six different beam thicknesses. As shown in FIG. 6, the larger the beam thickness, the larger the value of calibration data. This is so because the amount of scattered rays increases as the region of the patient P to be irradiated with X rays increases in size. The scattered ray amount increases because, as shown in FIGS. 7A and 7B, the larger the beam thickness, the larger the number of incident paths of scattered rays SX (indicated by the broken lines in FIGS. 7A and 7B). FIGS. 8A and 8B schematically illustrate the relationship between the size (a radius R and a length L) of the field of view FOV and the scattered ray amount. As depicted in FIGS. 8A and 8B, the scattered ray amount changes in accordance with the size of the patient P. In FIGS. 8A and 8B, the section of the X-ray detector 112 is a rectangle. However, this is merely an example, and the section can also be a circular arc (FIG. 19).

As described above, the six calibration data files corresponding to the six different beam thicknesses are acquired.

Figure 9:
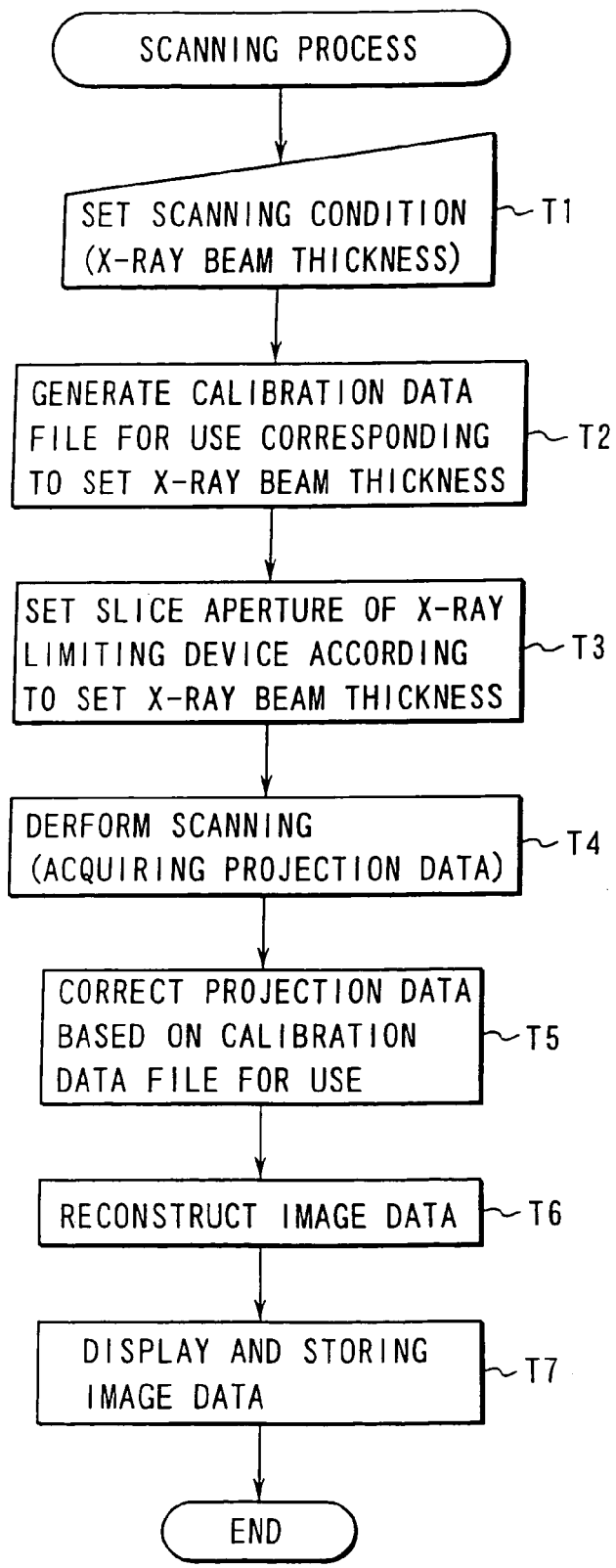
FIG. 9 is a flow chart showing the flow of an object scanning process in this embodiment.

FIG. 9 shows an actual scan procedure for the patient P. As in step T1, the beam thickness (or the size of FOV) is input in accordance with the purpose of examination from the input device 127.

This beam thickness can be set to an arbitrary integral multiple of a unit length of 1 mm as the pitch of the detecting elements, regardless of the six different, discrete beam thicknesses to which the six calibration data files correspond. Letting Xmax denote the beam thickness defined by the use region in the X-ray detector 112, a beam thickness Xt settable in this case can be expressed by 0<Xt≦Xmax. That is, the settable beam thickness Xt is substantially "arbitrary" within the range having Xmax as the upper limit, although the set pitch described above is restricted.

Figure 10A:
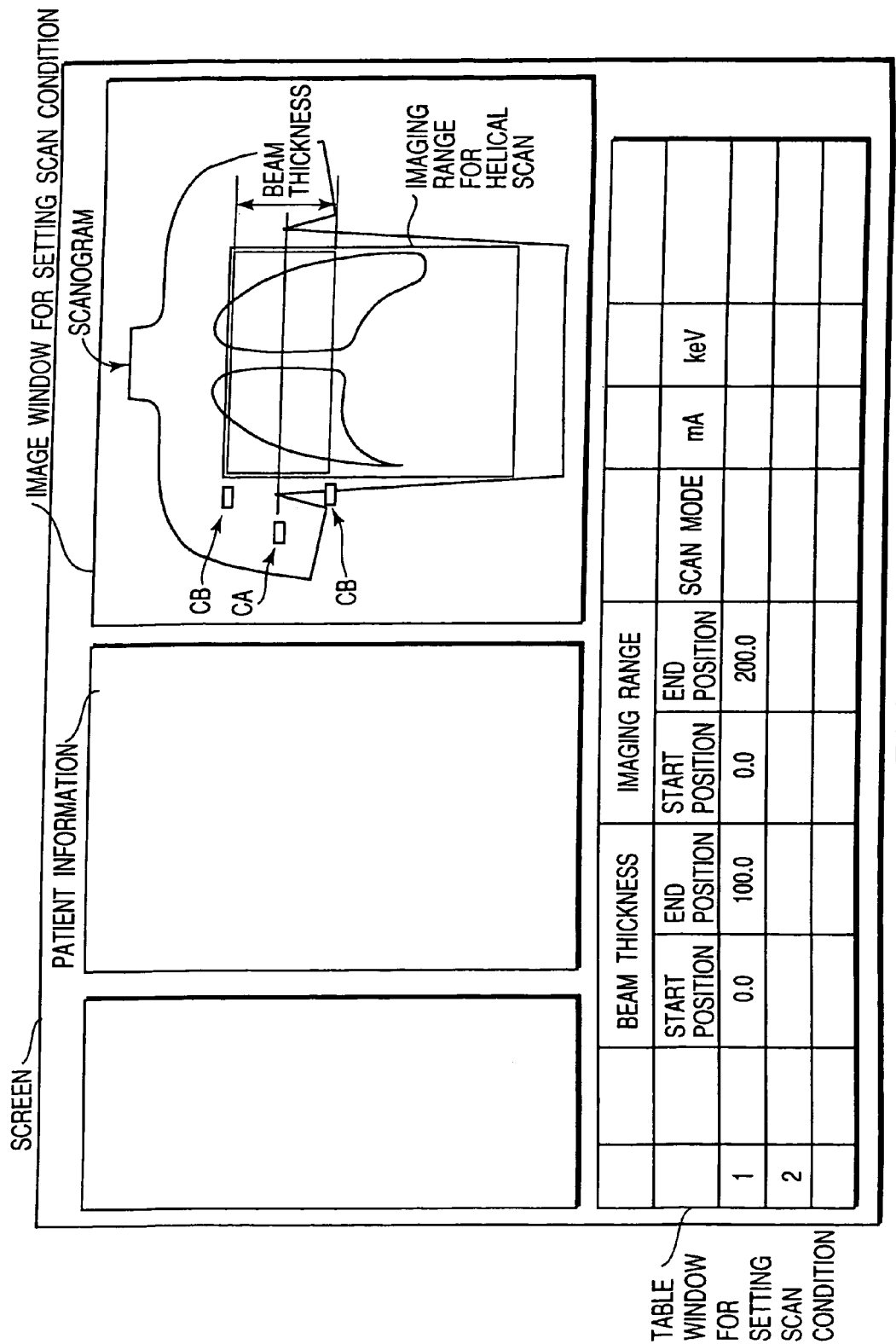
FIGS. 10A and 10B are views showing a beam thickness input window in a screen.

FIG. 10A shows a beam thickness setting window. The beam thickness setting window is displayed with a patient information window and a scan condition table window in a screen. Two types of cursors CA and CB are displayed on a scanogram in order to set a beam thickness. The cursor CA represents the centerline of the beam with respect to the slice direction. The two cursors CB represent two ends of the beam with respect to the slice direction. The operator manipulates a pointing device such as a mouse to move the cursor CA back and forth along the slice direction. This allows setting the beam center to a desired position. The operator manipulates the pointing device such as the mouse to one of the two cursors CB back and forth along the slice direction. The other cursor CB automatically moves upon movement of one cursor CB such that the distance between one cursor CB (one beam end) and the cursor CA (beam center) becomes equal to the distance between the other cursor CB (other beam end) and the cursor CA (beam center). This allows setting the beam thickness to a desired thickness. The numerical values in start/end position cells of a beam thickness column are changed automatically in accordance with the movements of the cursors CA and CB. Conversely the positions of cursors CA and CB are changed automatically in accordance with the newal of the numerical values.

Figure 10B:
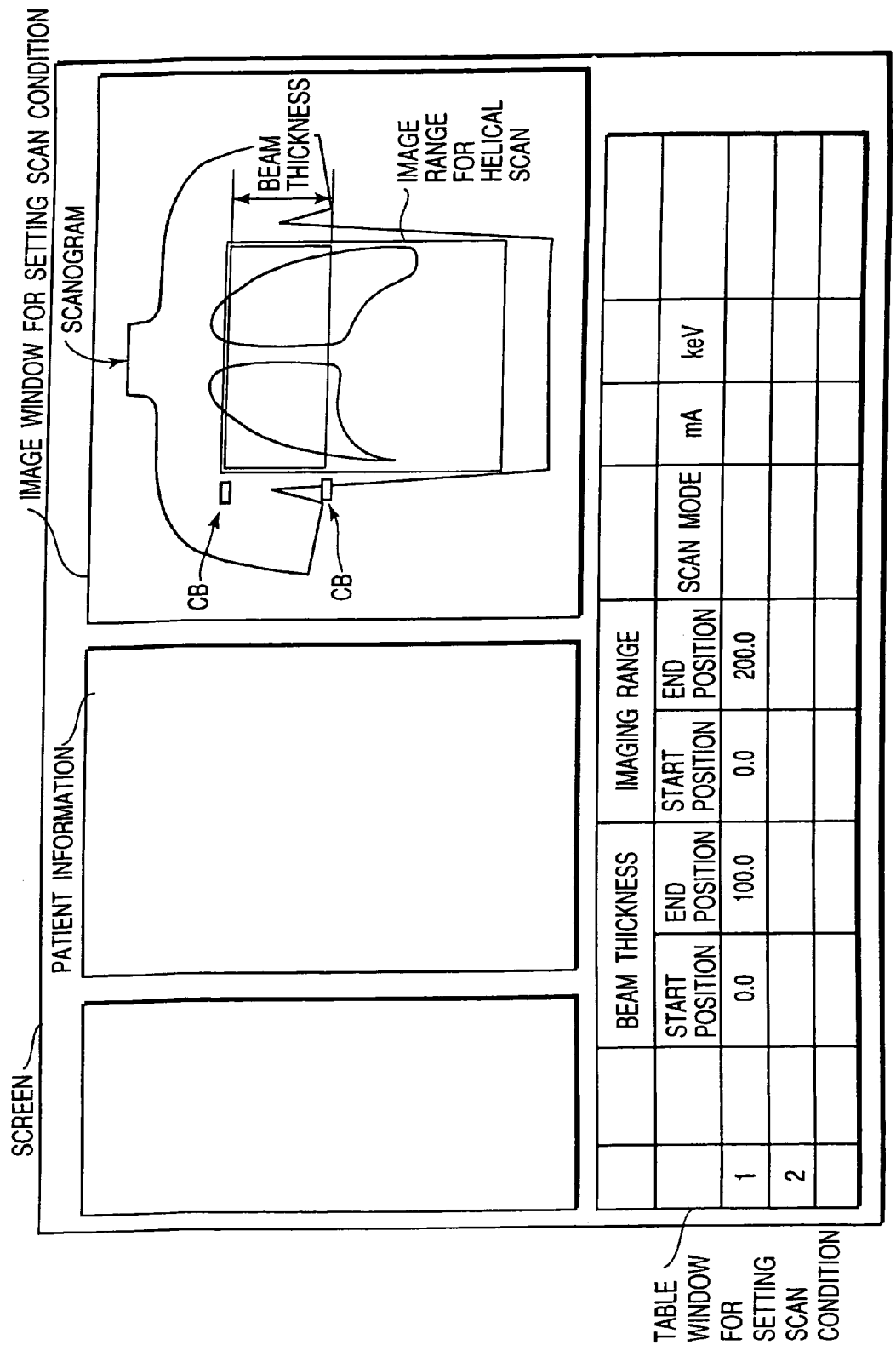

FIG. 10B shows another beam thickness setting window. The beam thickness setting window is displayed with a patient information window and a scan condition table window in a screen. According to this method, two cursors CB representing the two ends of a beam with respect to the slice direction are used in order to set a beam thickness. The operator manipulates the pointing device such as the mouse to move one cursor CB back and forth along the slice direction. The operator also manipulates the pointing device such as a mouse to move the other cursor CB back and forth along the slice direction. This allows setting the beam thickness to a desired thickness and the beam center to a desired position.

Next, as in step T2, on the basis of at least one calibration data file corresponding to the set beam thickness, a "calibration data file for use" to be used to correct raw data of the patient P is generated. The method of generating this calibration data file for use will be described later. This "generation" process is performed by the central control unit 121 described earlier. In step T3, a slice aperture of the limiting device 111c shown in FIG. 4 is set such that the set beam thickness is obtained.

As shown in steps T4 to T7, the patient P is irradiated with X-rays to acquire raw data, and the acquired raw data is corrected by the preprocessing unit 123. On the basis of projection data generated by the correction, the reconstructing unit 125 reconstructs volume data. From this volume data, the data processing unit 126 generates image data for display, such as a tomogram or a three-dimensional image. This image data for display is displayed on the image displaying unit 12D or stored in the storing unit 12M.

The correction process (step T5 in FIG. 9) that the preprocessing unit 123 performs for the raw data from the data acquisition system 122 by using the calibration data file for use will be described in detail below.

Figure 11:
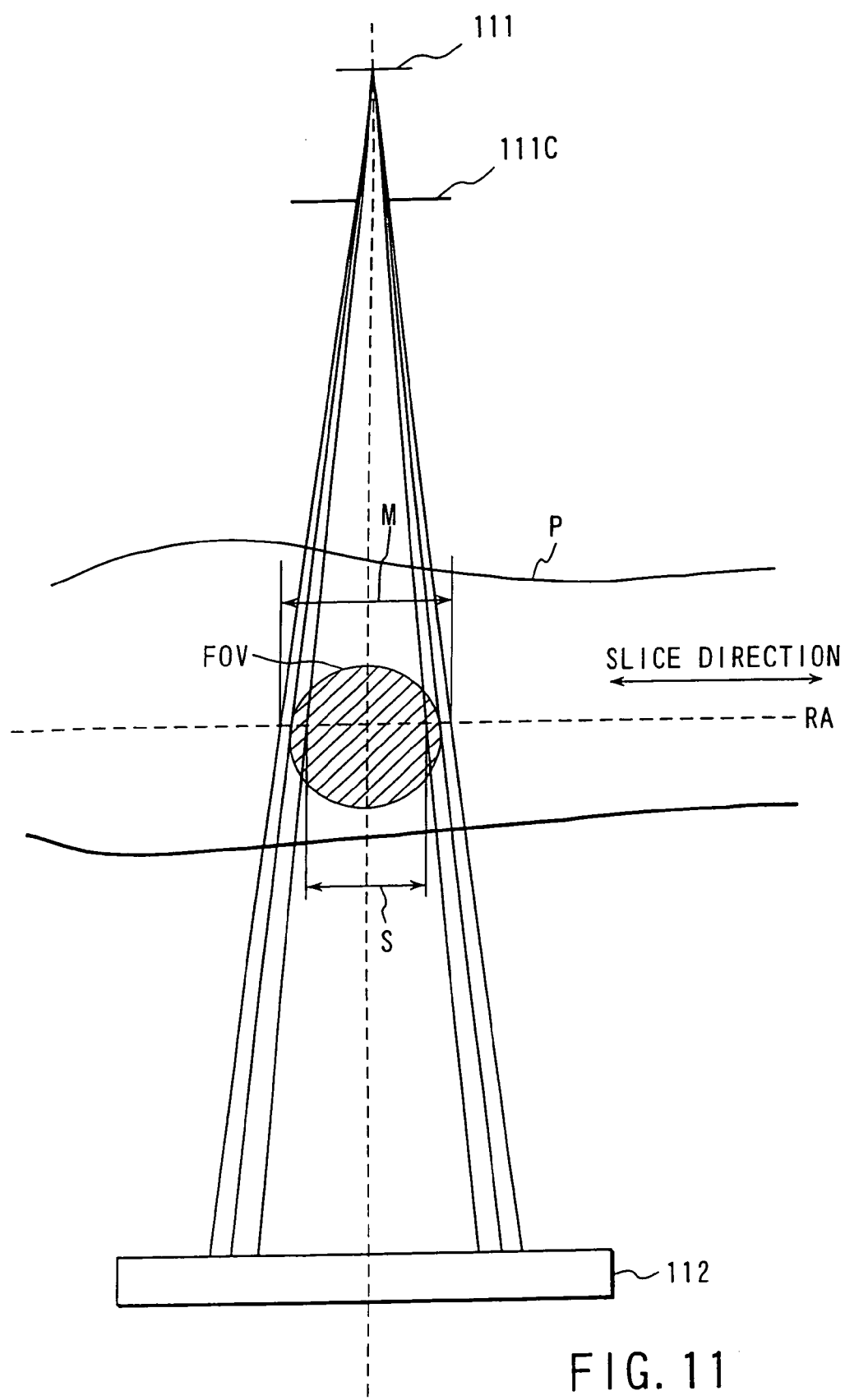
FIG. 11 is a view showing geometry when an object to be examined is scanned in this embodiment.

FIG. 11 shows an example of geometry during scanning of the patient P. The beam thickness is set as indicated by the thick line in FIG. 11. The set beam thickness does not match any of the six different beam thicknesses corresponding to the six calibration data files. In this example, the set beam thickness is intermediate between M and S. If no matching calibration data file exists, correction cannot be performed in conventional apparatuses. In the first place, beam thickness choices are limited to beam thicknesses corresponding to calibration data files. In this embodiment, however, a calibration data file for use which matches an actually set beam thickness is generated from at least one of the six different calibration data files described above (step T2 in FIG. 9).

As the method of generating the calibration data file for use, five different methods from the first to fifth methods are provided. The central control unit 121 can be equipped with one or all of these five methods. In the latter case, these five methods are selectively used in accordance with a designation by an operator. The five different methods of generating a calibration data file for use will be explained below in turn.

(First Method: Interpolation)

This first method obtains the aforementioned calibration data file for use by interpolation from at least one calibration data file selected in accordance with the set beam thickness from the six different existing calibration data files described above. As shown in FIG. 6, the values of these six different calibration data files increase as the beam thickness increases under the influence of scattered rays. However, it is known that the relationship between the scattered ray amount and the beam thickness is substantially a proportional relationship. Therefore, linear interpolation using the beam thickness as a parameter can be performed for each corresponding detecting element of the X-ray detector 112.

Figure 12:
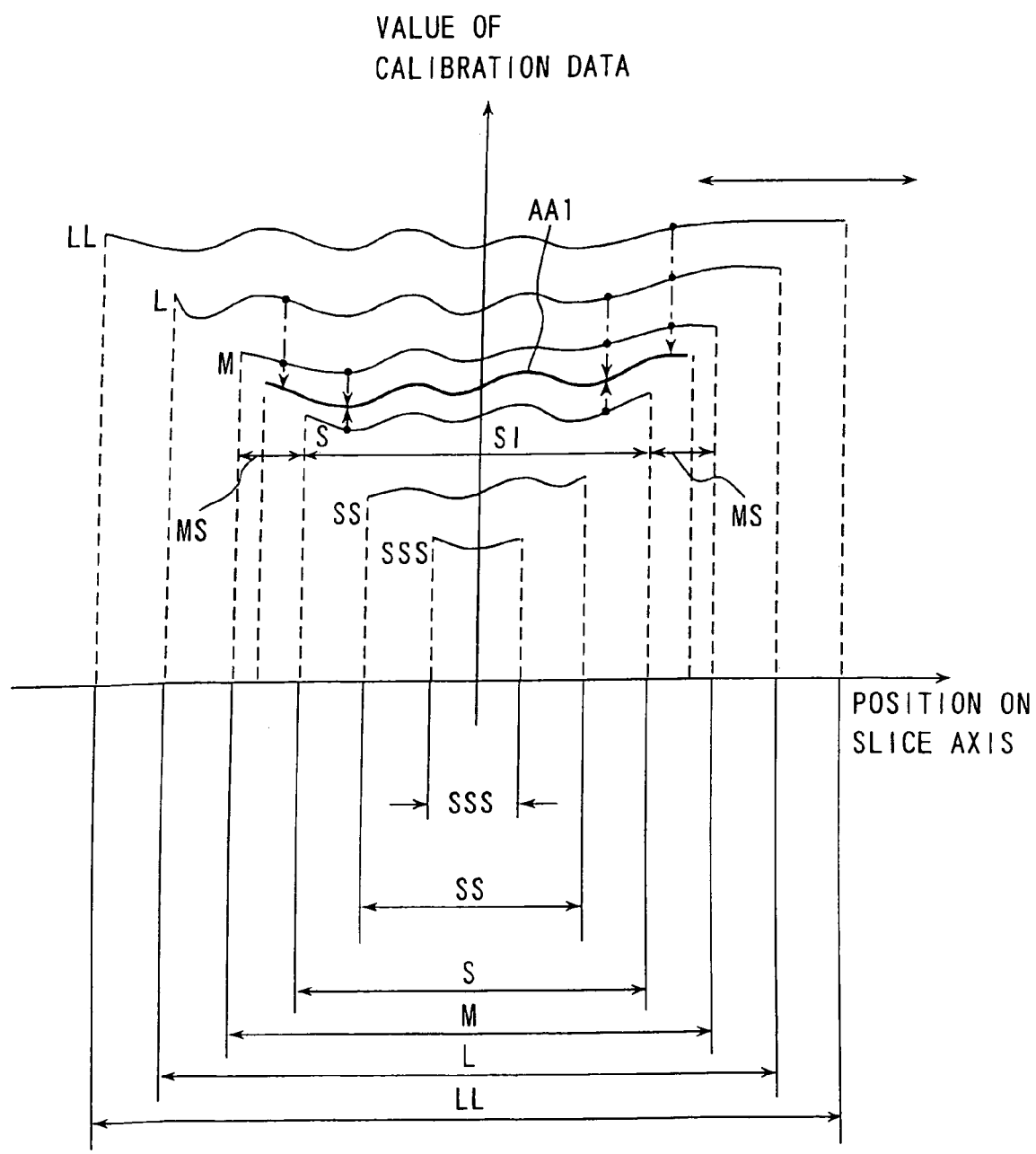
FIG. 12 is a view showing the first example of a method of generating a calibration data file for use corresponding to a set beam thickness in this embodiment.

For example, if the set beam thickness is between the M- and S-regions as shown in FIG. 11, two-point interpolation is performed using calibration data files of the M- and S-regions, as indicated by the alternate long and short dashed line in FIG. 12, for those detecting elements (in a region SI in FIG. 11) of the X-ray detector 112 which are inside the S-region. For detecting elements (in a region MS in FIG. 11) between the M- and S-regions, extrapolation is performed using calibration data files of the L- and M-regions, since there is no calibration data file of the S-region. By these interpolating processes, a calibration data file AA1 for use as shown in FIG. 12 is obtained.

In the present invention, as indicated by the alternate long and two short dashed line in FIG. 12, multi-point interpolation can also be performed instead of the two-point interpolation. That is, for detecting elements in the region SI described above, interpolation can be performed using three points on calibration data files of the L-, M-, and S-regions. For the region MS, interpolation can be performed using three points on calibration data files of the LL-, L-, and M-regions. Furthermore, in place of the above methods, interpolation can also be performed using all the six different calibration data files for, e.g., detecting elements in the region SI.

In the multi-point interpolation as described above, the number of points to be used in interpolation can be properly determined from the relationship between the effect and the processing amount. Also, as described above, FIG. 12 shows examples of two-point interpolation and three-point interpolation. However, this simply means that the two methods are illustrated in one figure for the sake of convenience of explanation. In practice, therefore, the calibration data file AA1 for all beam thicknesses is generally obtained by two-point interpolation or three-point interpolation alone.

It is, however, exceptionally possible in some cases to use two-point interpolation and three-point or multi-point interpolation at the same time. A case is, e.g., when it is desirable to acquire an image having higher accuracy in a portion near the ordinate in FIG. 12, i.e., in a central portion of the X-ray detector 112, than in other portions. In this case, it is possible to perform three-point interpolation near the ordinate and two-point interpolation in the other portions. The present invention has no intention to positively exclude these forms.

Figure 13:
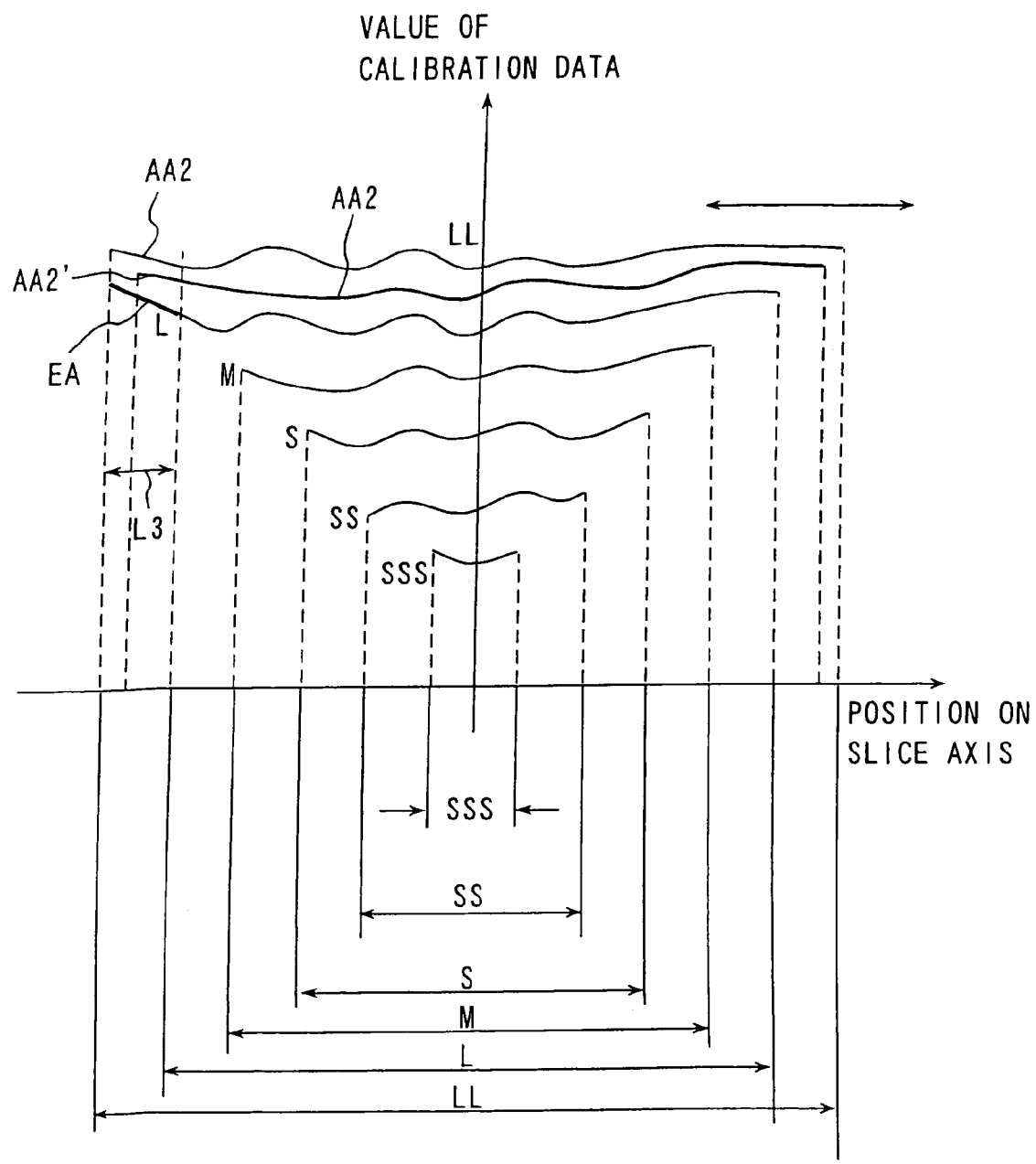
FIG. 13 is a supplementary view of FIG. 12.

Also, if the set beam thickness is present between the LL- and L-regions (a region L3) as shown in FIG. 13, it is impossible to obtain calibration data files at a plurality of points necessary for interpolation for obtaining a calibration data file AA2 for use. This basically makes interpolation impossible to perform. The simplest method in a case like this is to, e.g., use a calibration data file concerning the LL-region directly as a calibration data file for use.

In the processing as described above, however, as shown in FIG. 13, a calibration data file concerning the beam thickness inside the L-region and a calibration data file concerning the beam thickness in the region L3 become discontinuous. This situation is not preferred because it may cause an artifact on the reconstructed image. In this method, therefore, the following method can be used instead of the above one.

That is, as shown in FIG. 13, it is possible to use information contained in an edge portion of a calibration data file pertaining to the L-region, i.e., to use a differential coefficient, or to obtain an extrapolation point on the basis of an output value near the edge. In this manner, a calibration data file (to be referred to as an "extended calibration data file" hereinafter) EA which is extended to smoothly connect to the edge portion is formed. When two-point interpolation is performed using this extended calibration data file EA and a calibration data file of the LL-region, a calibration data file AA' for use having higher accuracy is obtained. In this method, no such discontinuous portion as mentioned above is produced.

This method of forming the extended calibration data file EA is generally applicable to a portion where the combination of calibration data files for use in interpolation changes, i.e., to an edge portion of each of the six different calibration data files. For example, when the two-point interpolation explained with reference to FIG. 12 is to be performed, the process in the region MS is done by performing extrapolation using calibration data files of the L- and M-regions in the above method. Instead, it is possible to form an extended calibration data file concerning a calibration data file of the M-region on the basis of an edge portion of this calibration data file, and perform two-point interpolation in the same manner as in the region SI. This method can suppress the generation of an artifact caused by a difference in a portion where these regions connect.

(Second Method: Substitution)

In this second method, one calibration data file selected by predetermined standards from the six different calibration data files described above is substituted as most appropriate for a calibration data file for the set beam thickness. That is, a previously acquired calibration data file is directly used without performing any interpolation unlike in the above first method.

Figure 14:
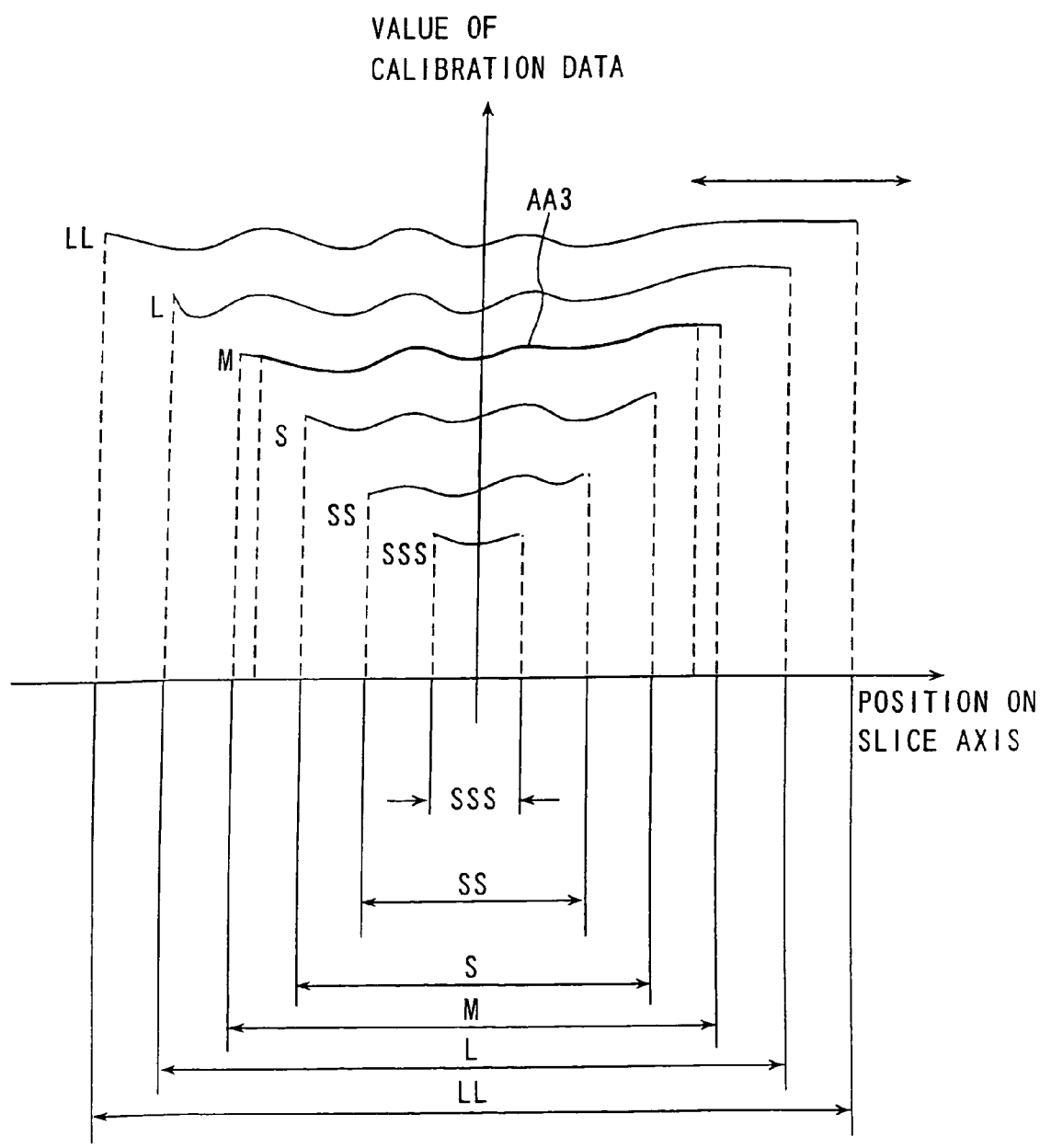
FIG. 14 is a view showing the second example of the method of generating a calibration data file for use corresponding to a set beam thickness in this embodiment.

For example, if the set beam thickness is present between the M- and S-regions as shown in FIG. 11, a calibration data file of the M-region is selected and used as a calibration data file AA3 for use as shown in FIG. 14. Examples of standards for selecting one of the six different calibration data files are the following items.

First, to effectively perform calibration, calibration data files are required for all detecting elements from which data is acquired by scanning. Therefore, a calibration data file obtained by a beam thickness smaller than when the patient P is scanned cannot be used. That is, in the above example, the data of the M-, L-, and LL-regions are used without using the calibration data file of the S-region. Second, the scattered ray amount changes in accordance with the beam thickness as described earlier. Hence, data obtained under conditions closest to the beam thickness when the patient P is scanned is suitable as a calibration data file to be selected.

From the foregoing, it is most preferable to use that calibration data file pertaining to the smallest beam thickness, which is one of calibration data files pertaining to beam thicknesses larger than the beam thickness when the patient P is scanned. In the example shown in FIG. 14, a calibration data file of the M-region is used.

Whether to use interpolation of the first method or substitution of the second method is suitably determined by taking account of the performance of the X-ray CT scanner 1 or the central control unit 121. Alternatively, the X-ray CT scanner 1 according to the present invention can hold both the above two processes such that either process can be practiced. In this case, an operator of the apparatus can appropriately select a desired process.

Generally speaking, the interpolation process described above enhances the effect of reducing the number of calibration data files which must be acquired in advance in accordance with FIG. 3. On the other hand, the substitution process has an effect of making this interpolation process unnecessary.

(Third Method: Processing Using Calibration Data File Edge Portion)

This third method is characterized in that a calibration data file for use is prepared by using an edge portion of a calibration data file, or by using the method of forming the extended calibration data file EA by focusing attention on this edge portion, described in the first method. In the following explanation, a case in which the set beam thickness is present between the M- and S-regions as shown in FIG. 11 is taken as a representative example. Also, figures to be referred to in the following explanation are simplified by showing only calibration data files of the M- and S-regions.

Figure 15:
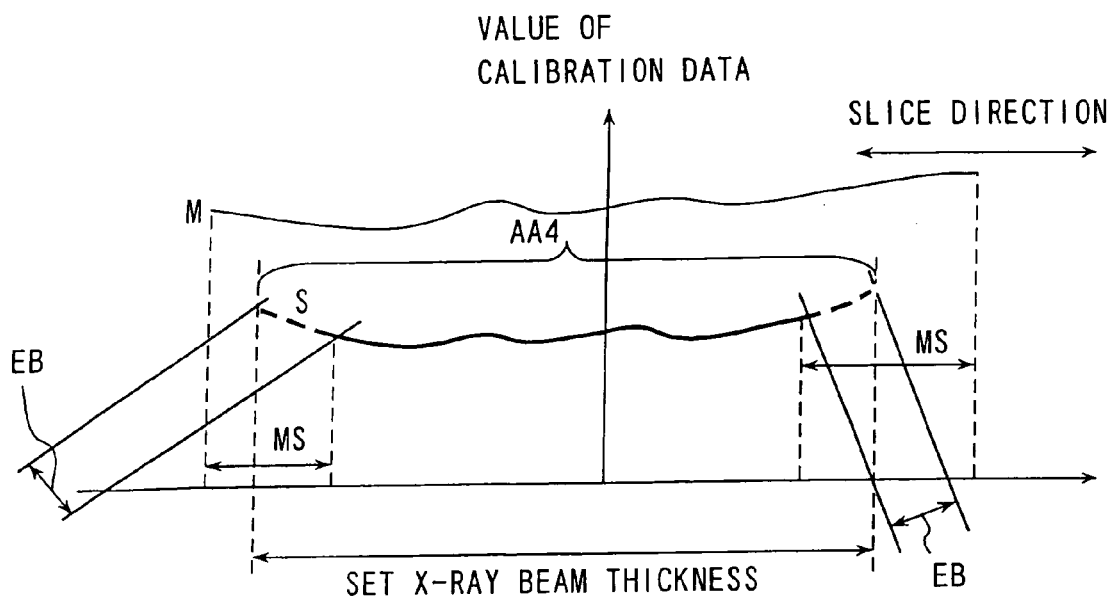
FIG. 15 is a view showing the third example of the method of generating a calibration data file for use corresponding to a set beam thickness in this embodiment.

First, as a simple method, the extended calibration data file described above can be directly used as a calibration data file for use. That is, as shown in FIG. 15, an extended calibration data file EB based on an edge portion of a calibration data file of the S-region is formed. In addition, a calibration data file AA4 for use is prepared by connecting this extended calibration data file EB and the calibration data file of the S-region.

This processing method is basically similar to the concept of the substitution process mentioned above. The difference is that a calibration data file of the M-region is used in the substitution process (FIG. 14), but a calibration data file of the S-region is basically used in this process. This is possible because the extended calibration data file EB is formed.

Figure 16:
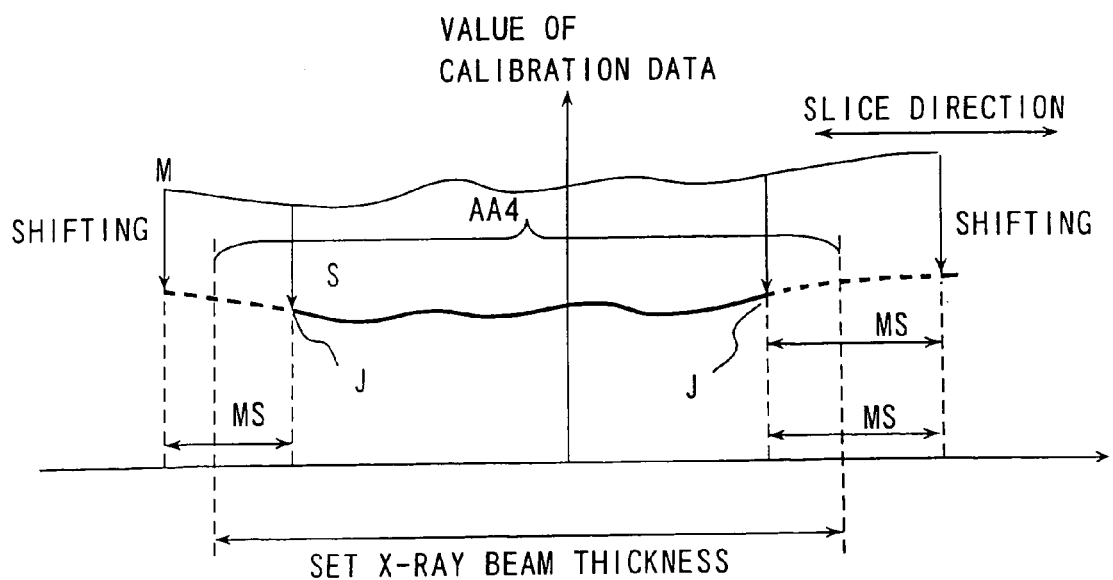
FIG. 16 is a view showing the fourth example of the method of generating a calibration data file for use corresponding to a set beam thickness in this embodiment.

As a simpler method, an existing calibration data file form (curve form) is directly used without forming any extended calibration data file, but caution is exercised on an edge portion. That is, as shown in FIG. 16, a calibration data file in the region MS is shifted down to meet the output value of a calibration data file of the S-region. A connecting point (≈edge portion) J between the shifted calibration data file (of the M-region) in the region MS and the calibration data file of the S-region is subjected to processing by which the two output values continue. This processing has no big difference from the concept of the process of obtaining an extended calibration data file. Note that as a calibration data file AA4 for use, only the corresponding region need be extracted.

Figure 17:
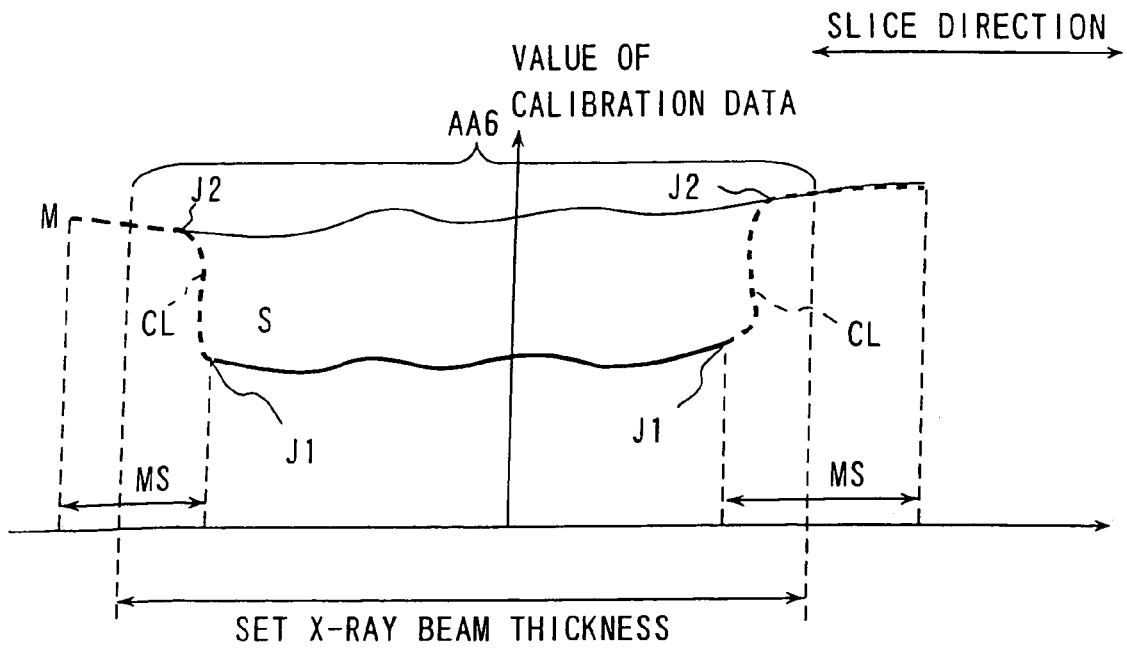
FIG. 17 is a view showing the fifth example of the method of generating a calibration data file for use corresponding to a set beam thickness in this embodiment.

Still another method is to make the best use of the form of a calibration data file without "shifting" the calibration data file. For example, as shown in FIG. 17, a calibration data file (to be referred to as a "connecting calibration data file" hereinafter) CL is prepared which connects an edge portion of a calibration data file of the S-region to a calibration data file of the M-region. One end of this connecting calibration data file CL is smoothly connected to a portion J1 near the edge portion of the calibration data file of the S-region. The other end of the connecting calibration data file CL is smoothly connected to a portion J2 near the edge portion in a position where the calibration data file curve of the M-region intersects the boundary defining the S-region. Note that as a calibration data file AA6 for use, only the corresponding region is extracted similar to FIG. 16.

The processing method as described above can prevent the generation of a discontinuous portion as explained with reference to FIG. 13 in the first method.

Also, this third method does not use a calibration data file concerning a region larger than the set beam thickness, unlike in the substitution process of the second method. That is, for a lacking portion (the region MS in FIG. 15 or 17), the extended calibration data file EB is used (FIG. 15), a calibration data file concerning a region larger than the set beam thickness is used after being shifted (FIG. 16), or a calibration data file concerning a region larger than the set beam thickness is used while the connecting calibration data file CL is formed and used (FIG. 17). This makes it possible to use a calibration data file of a region smaller than the set beam thickness.

The use of a calibration data file of a region smaller than the beam thickness is advantageous when, in the examples shown in FIGS. 15 to 17, the beam thickness is close to the size of the S-region and far from the size of the M-region. The reason requires no explanation. In the above second method, however, a calibration data file of the M-region is prepared as a calibration data file for use even in a case like this. The significance of this third method is confirmed in this respect.

That is, from this viewpoint it is preferable to use a calibration data file pertaining to a beam thickness closest to the set beam thickness.

To make the above operation effective, it is necessary to determine which of the six different beam thicknesses (="LL" to "SSS") corresponding to the six different existing calibration data files the set beam thickness is close to.

This is done simply by comparing practical numerical values of the beam thicknesses, i.e., "LL" to "SSS", corresponding to the six different existing calibration data files previously acquired, with a practical numerical value of the set beam thickness. Consequently, it is readily possible to determine which of "LL" to "SSS" the set beam thickness is close to.

Figure 18:
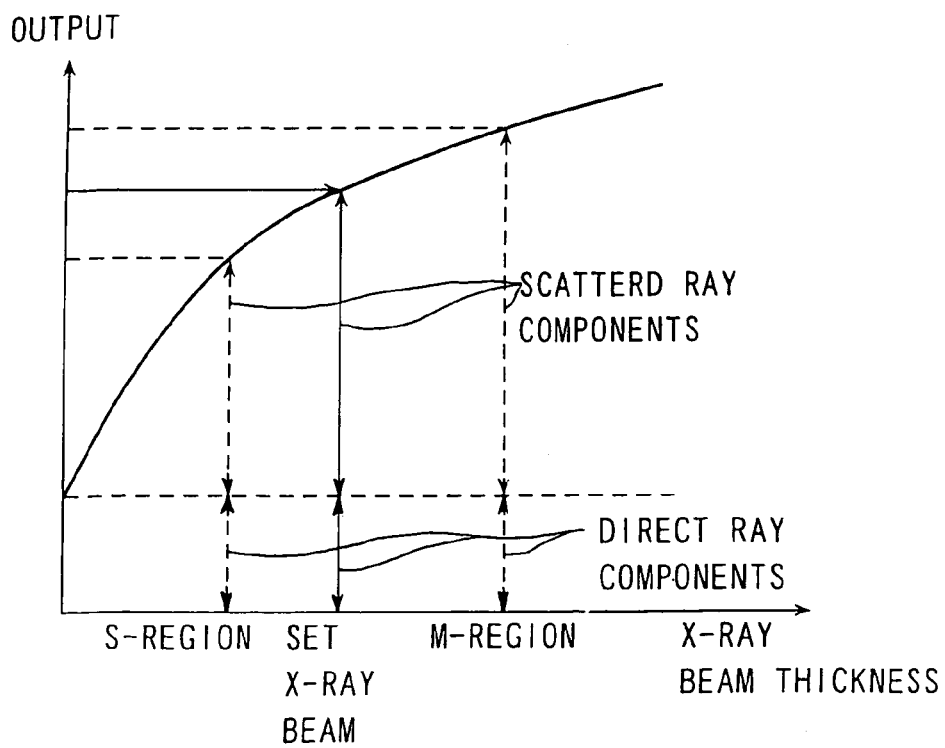
FIG. 18 is a view showing a method of determining a calibration data file concerning a beam thickness closest to a set beam thickness in this embodiment.

Alternatively, as shown in FIG. 18, it is also possible to perform processing which conceptually uses a graph in which the output from a certain detecting element of the X-ray detector 112 is plotted on the ordinate, and the beam thickness is plotted on the abscissa.

In this graph, the sizes (=beam thicknesses) and the outputs of the S- and M-regions are already known by the calibration data file acquisition process shown in FIG. 3. Also, an appropriate number of outputs from the certain detecting element with respect to a beam thickness between the S- and M-regions are acquired beforehand. As a consequence, the graph shown in FIG. 18 can be formed.

By referring to the output result obtained by the set beam thickness for the certain detecting element concerning this graph, whether the set beam thickness is close to the S- or M-region is determined (see arrows in FIG. 18). On the basis of this result, various processes explained in this third method are performed if the set beam thickness is close to the S-region, and the substitution process explained in the second method is performed if the set beam thickness is close to the M-region. That is, processing using a calibration data file concerning a beam thickness close to the set beam thickness can be performed.

This processing using FIG. 18 is advantageous because, as shown in FIG. 18, the outputs of a plurality of regions do not strictly have a proportional relationship in some instances. That is, if the beam thickness and the output have a nonlinear relationship as shown in FIG. 18, it is difficult for the simple comparison described above to accurately determine which region the set beam thickness is close to. However, the processing herein mentioned makes this possible. Note that the graph shown in FIG. 18 is formed for a "certain detecting element". However, the present invention is not limited to this example. For example, a graph as shown in FIG. 18 can also be formed for "several detecting elements (specific detecting elements) selected with high symmetry from the X-ray detector 112", or for a "plurality of detecting elements (specific detecting elements) in the same channel".

In this third embodiment, the set beam thickness is present between the M- and S-regions. However, other cases (e.g., a case in which the set beam thickness is present between the L- and M-regions) can also be exactly similarly processed.

In step T5 of FIG. 9, the calibration data files AA1 to AA6 for use acquired by the first to third methods as described above are subjected to actual correction for scan data. It is obvious that this correction process using the calibration data files AA1 to AA6 for use can appropriately correct the sensitivity of the X-ray detector 112.

(Fourth Method: Scattered Ray Correction)

This fourth method is characterized in that variously settable beam thicknesses can be corrected by applying a scattered ray correction process. As described previously, scattered rays are excessively detected X-ray components other than direct X rays. The larger the beam thickness and the larger the diameter of the patient P, the larger the amount of scattered rays (FIGS. 7A, 7B, 8A, and 8B).

"Scattered ray correction" is the process of excluding such scattered rays from projection data, and obtaining projection data consisting substantially primarily of direct X rays. This scattered ray correction process can be performed by using, e.g., the preprocessing unit 123, the central control unit 121, or a dedicated arithmetic unit (to be referred to as a second correcting means hereinafter). As the scattered ray correction process of this fourth method, a method disclosed in, e.g., Jpn. Pat. No. 1631264 or Jpn. Pat. Appln. KOKAI Publication No. 11-89827 can be used.

The scattered ray correction process disclosed in Jpn. Pat. Appln. KOKOKU Publication No. 1631264 will be briefly described below. That is, as shown in FIG. 19, an X-ray diagnostic apparatus of this publication includes an X-ray shielding means XS. This X-ray shielding means XS is constructed by arranging X-ray shielding members such as lead pieces XSB at equal intervals on an X-ray transmitting member XSA obtained by shaping, e.g., acrylic resin into the form of a thin plate. This X-ray shielding means XS can move as indicated by arrows shown in FIG. 19, and can make X-rays emitted from an X-ray tube 111 shielded or unshielded with respect to an X-ray detector 112. Note that X-rays are, of course, shielded or unshielded at the positions of the lead pieces XSB.

When this X-ray shielding means XS is positioned in the field of irradiation, the X-ray diagnostic apparatus can acquire X-ray shielded data. During the acquisition of this X-ray shielded data, no X-rays are directly incident on detecting elements corresponding to the positions of the lead pieces XSB. So, the resulting output (scattered ray data) reflects the presence of scattered rays. After that, therefore, on the basis of the relationship between the positions of the lead pieces XSB and the scattered ray data corresponding to the individual positions, the distribution (scattered ray intensity data) of scattered ray intensity on the entire surface (=all detecting elements) of the X-ray detector 112 can be calculated. According to the publication, this is done by data interpolation using a sampling function.

By calculating a difference between the scattered ray intensity data thus obtained and original image data obtained by positioning the X-ray shielding means XS outside the irradiation field, projection data excluding the influence of scattered rays is obtained.

Figure 20:
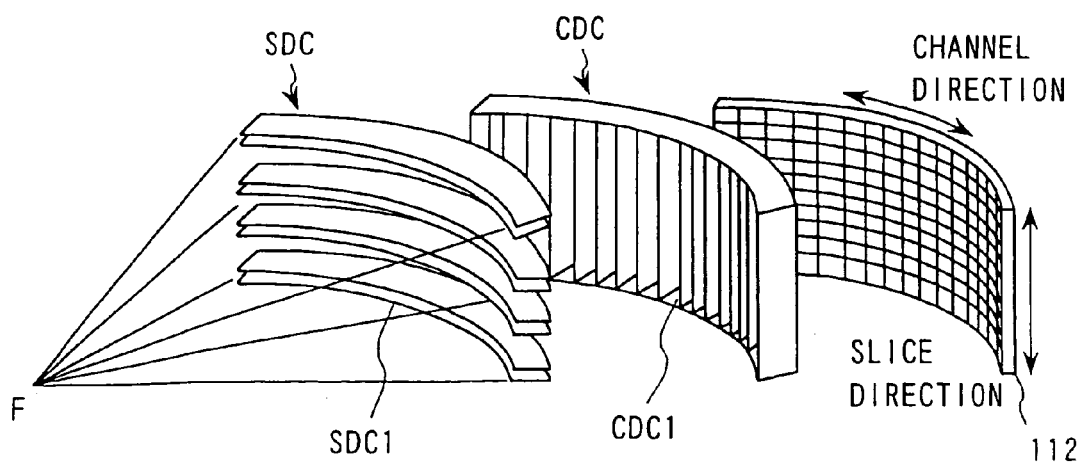
FIG. 20 is a view showing a system configuration for practicing a scattered ray correction process, disclosed in Jpn. Pat. Appln. KOKAI Publication No. 11-89827.

The scattered ray correction process disclosed in Jpn. Pat. Appln. KOKAI Publication No. 11-89827 is substantially as follows. That is, as shown in FIG. 20, an X-ray CT scanner of this publication includes a channel-direction collimator CDC and a slice-direction collimator SDC on the front surface of an X-ray detector 112. The channel-direction collimator CDC prevents scattered rays in a channel direction from entering the X-ray detector 112. The slice-direction collimator SDC prevents scattered rays in a slice direction (parallel to the axial direction of the patient P) from entering the X-ray detector 112. Collimator plates CDC1 are densely arranged in the channel-direction collimator CDC. Collimator plates SDC1 are "sparsely" arranged in the slice-direction collimator SDC.

Figure 21A:
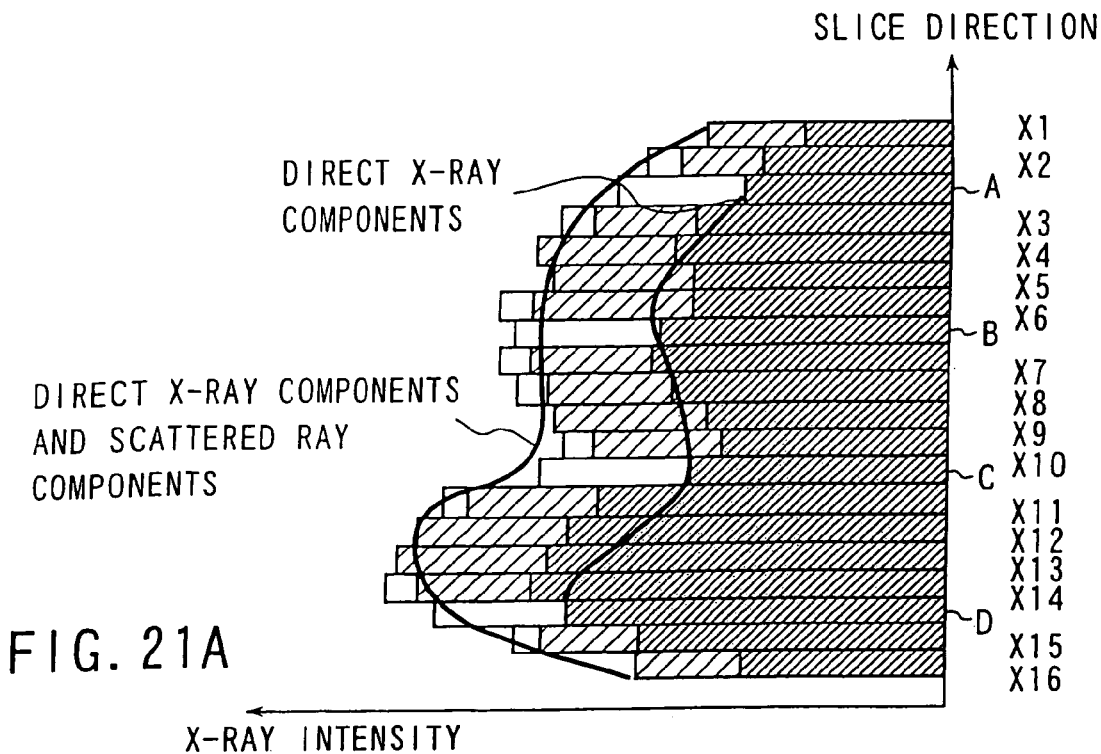
FIGS. 21A and 21B are graphs showing the forms of X-ray components obtained by an X-ray detector in the system configuration shown in FIG. 20.
Figure 21B:
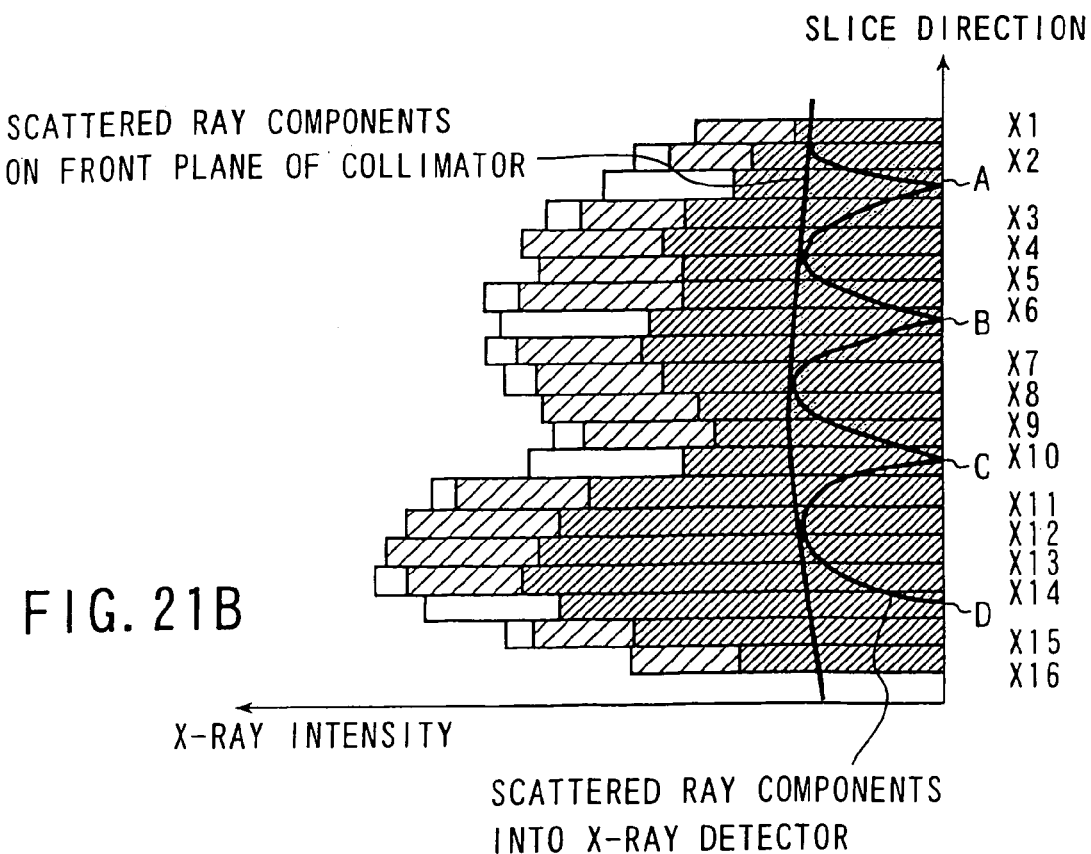

In this X-ray CT scanner, as shown in FIGS. 21A and 21B, the action of the slice-direction collimator SDC (physically) removes scattered rays only in the positions of the collimator plates SDC1. Consequently, detecting elements A to D of the X-ray detector 112 immediately below these positions detect only direct X rays (see "dense hatched portions" in FIGS. 21A and 21B).

Detecting elements X2 and X3, X6 and X7, X10 and X11, and X14 and X15 on the two sides of the detecting elements A, B, C, and D, respectively, detect X rays from which scattered rays are slightly removed but which still contain remaining scattered ray components. Remaining detecting elements X1, X4, X5, X8, X9, X12, X13, and X16 detect X rays (direct X rays+scattered rays) from which no scattered ray components are removed at all (in FIGS. 21A and 21B, "broken-line portions" indicate physically removed scattered rays, and "sparse hatched portions" indicate detected scattered rays).

In the above publication, from the differences between these modes, the distribution of direct ray components is estimated on the basis of the outputs from the detecting elements A to D, and the distribution of direct ray components and scattered ray components is estimated on the basis of the outputs from the detecting elements X1, X4, X5, X8, X9, X12, X13, and X16 (FIGS. 21A and 21B). By subtracting the former from the latter, the distribution of only scattered rays on the front surface of the collimator can be obtained. By multiplying this scattered ray distribution by a previously calculated removal ratio, a scattered ray amount incident on each detecting element can be estimated.

By subtracting the thus estimated scattered ray amount from actual scan data, projection data from which the influence of scattered rays is eliminated is obtained. The "removal ratio" is the ratio of the scattered ray amount removed when the slice-direction collimator SDC is present to the total scattered ray amount when this collimator SDC is absent.

In this fourth method, the above scattered ray correction is first performed in the calibration data file acquisition process explained with reference to FIG. 3. Note that this calibration data file acquisition is performed only for a calibration data file concerning the maximum beam thickness determined by the size of the X-ray detector 112. That is, in the example shown in FIG. 4, only a calibration data file concerning the LL-region is acquired. Therefore, in the calibration data file acquisition process shown in FIG. 3, the processing in step S5 is omitted.

The actual scan conditions, however, include not only the beam thickness but also conditions such as the tube voltage of the X-ray tube 111. Hence, although "only a calibration data file pertaining to the LL-region is acquired", a necessary number of calibration data files must be acquired for the other parameters. That is, it is necessary to acquire, e.g., a "calibration data file for a tube voltage v [V] of the X-ray tube 111 when the beam thickness is the LL-region", and a "calibration data file for a diameter d [m] of the patient P when the beam thickness is the LL-region". In this example, however, as already mentioned above, only the beam thickness is taken into consideration as the scan condition.

The timing at which scattered ray correction is performed for the acquired calibration data file of the LL-region is between steps S3 and S4 in FIG. 3. In this way, the scattered-ray-corrected calibration data file is stored (step S4 in FIG. 3).

Subsequently, the actual patient scanning process explained with reference to FIG. 9 begins. As described previously, a beam thickness is freely set at a fine pitch (steps T1 and T3 in FIG. 9), and data of a minimum necessary region of the patient P is acquired. A calibration data file prepared in step T2 of FIG. 9, i.e., a calibration data file for use in this fourth method, is naturally the scattered-ray-corrected calibration data file concerning the LL-region.

In step T5 of FIG. 9, the preprocessing unit 123 performs various correcting processes and scattered ray correction for the acquired patient scan data. Subsequently, the sensitivity of the X-ray detector 112 is corrected by using the scattered-ray-corrected data file (calibration data file for use) related to the LL-region on this scattered-ray-corrected scan data.

In this processing, sensitivity correction is performed by using the data (the scattered-ray-corrected calibration data file and scan data) from which the influence of scattered rays is eliminated by scattered ray correction. This eliminates the problem of the difference between scattered ray amounts produced by the difference between the beam thickness when calibration data files are acquired and that when the patient is scanned. As a consequence, a highly accurate image having little artifact is obtained.

In the above forth method, outlines of Jpn. Pat. No. 1631264 and Jpn. Pat. Appln. KOKAI Publication No. 11-89827 are explained as scattered ray correction processes. In the present invention, however, it is basically possible to use scattered ray correction based on any methods in addition to the above two scattered ray correction processes. In any case, the function and effect described above are achieved.

(Fifth Method: Combined Use of Scattered Ray Correction and Correction Process Based on Several Different Calibration Data Files)

This fifth method is characterized by combining the interpolation process, the substitution process, and the processing using a calibration data file edge portion described in the first, second, and third methods, with the scattered ray correction process described in the fourth method. In the following description, the combination of the interpolation process of the first method and the scattered ray correction process will be explained.

In this fifth method, similar to the first method described above, a plurality of different calibration data files concerning a predetermined beam thickness are acquired. Each of these calibration data files is subjected to scattered ray correction in the same manner as in the fourth method, and stored (the processing shown in FIG. 3 including scattered ray correction is performed).

The procedure shown in FIG. 9 then starts. In accordance with the scan condition (i.e., the "beam thickness" in this method) of the patient, the scattered-ray-corrected calibration data files are interpolated to estimate a calibration data file for use of patient scan data (see step T2 in FIG. 9 and the description in the first method). Scattered ray correction is also performed for the patient scan data as in the fourth embodiment. Sensitivity correction is performed for the thus obtained scattered-ray-corrected scan data by using the "calibration data file for use" based on the several different scattered-ray-corrected calibration data files estimated above (step T5 in FIG. 9).

This processing can simplify the scattered ray correction process. That is, in this fifth method, the interpolation process in the first method and the scattered ray correction process in the fourth method, both of which are proven to be effective in appropriately correcting a variously settable beam thickness, are performed in combination. This can relatively alleviate the duties to be fulfilled by the scattered ray correction process. This simplification of the scattered ray correction process is sometimes necessary depending on, e.g., the scheme of scattered ray correction and the weight, time, and the like of the correction process.

Also, in the above fifth method, a highly accurate image having little artifact is obtained for the same reason as above, even when the accuracy of scattered ray correction is low.

As has been described above, when the various processes explained as the first to fifth methods are performed, an appropriate calibration data file for use for a variously settable beam thickness can be obtained only by acquiring one or several different calibration data files. Basically, therefore, accurate sensitivity correction can be performed whatever the beam thickness is set.

Accordingly, in these methods, usable beam thicknesses are not limited unlike in conventional methods, so the beam thickness can be freely set. As a consequence, the patient P is not unnecessarily exposed to X rays.

In the first to third methods and the fifth method, six different calibration data files from "LL" to "SSS" are prepared for predetermined beam thicknesses. However, the present invention is not restricted to this form. Basically, any number of different calibration data files can be prepared. Also, in the methods except for the first method in which interpolation is performed, the processing can be performed in principle only by acquiring a calibration data file for "one" beam thickness.

Generally speaking, however, the first method can infinitely perform the processing for any beam thickness in principle, because interpolation is performed. Therefore, the number of calibration data files to be prepared can be small. In the second and third methods, however, it is preferable to prepare a larger number of calibration data files than in the first method.

The present invention is most suitably applicable to a so-called cone-beam X-ray CT scanner. However, it is of course also possible to apply the present invention to a "multi-slice X-ray CT scanner" described in "2 Description of the Related Art".

Furthermore, it is favorable to apply the following modification to the form of practicing the "scattered ray correction processes" described in the fourth and fifth methods.

(Determination of Propriety of Scattered Ray Correction Process)

This scattered ray correction process is characterized in that whether to perform scattered ray correction, or the amount or intensity (intensity of the degree of correction) of scattered ray components to be actually subtracted, is determined in accordance with a difference between set beam thicknesses and the like, for the fourth and fifth methods using scattered ray correction.

As already described several times, the scattered ray amount strongly depends upon the scan conditions, particularly the beam thickness and the diameter of the patient P; the larger the beam thickness and the larger the diameter of the patient P, the larger the scattered ray amount (FIGS. 7A, 7B, 8A, and 8B).

Conversely speaking, the influence of scattered rays is not so large if the beam thickness or the patient size (equivalent to the imaging region of an axial section as a scan condition) is small.

Accordingly, when the beam thickness or the patient size is used as a parameter, it is possible to determine whether to perform scattered ray correction, or to determine the amount or intensity of scattered ray components to be actually subtracted. More specifically, if the beam thickness or the patient size is large, the scattered ray amount increases, so scattered ray correction is performed or the amount of intensity of scattered ray components to be actually subtracted is increased. In contrast, if the beam thickness or the patient size is small, the scattered ray amount reduces, so no scattered ray correction is performed or the amount or intensity of scattered ray components to be actually subtracted is decreased.

The "amount or intensity of scattered ray components to be actually subtracted" described above can be determined by multiplying so-called "raw" scattered ray components ("scattered ray intensity data" in Jpn. Pat. No. 1631264, and an "estimated scattered ray amount" calculated by removal ratio multiplication in Jpn. Pat. Appln. KOKAI Publication No. 11-89827), purely calculated or estimated, by an appropriate proportional coefficient a. As is evident from the above explanation, the proportional coefficient a can be 0<a<1 or a≧1.

This processing can prevent the occurrence of abuses when scattered ray correction is performed although the necessity of the process is weak. "Abuses" herein mentioned simply include a prolonged operation time caused by the scattered ray correction process, and also mean a case as shown in FIG. 22.

Figure 22:
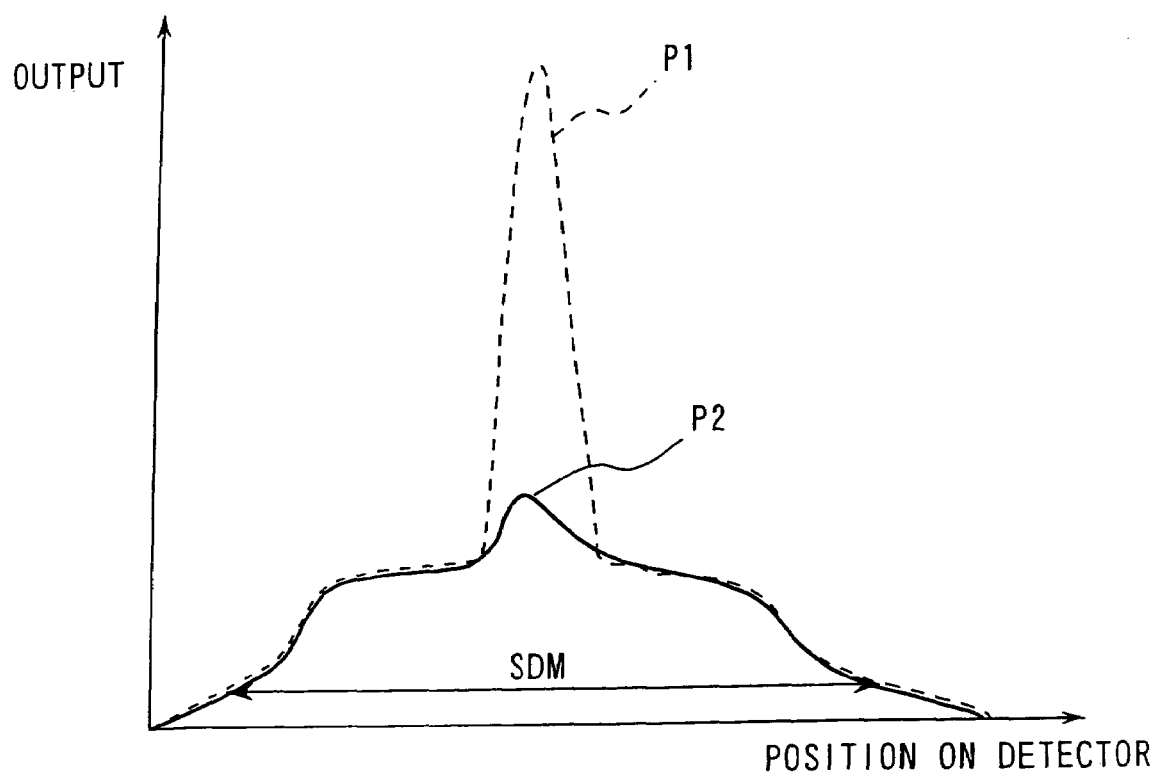
FIG. 22 is a view for explaining a status in which it is more advantageous not to practice a scattered ray correction process.

That is, when X-ray intensity as indicated by the broken line in FIG. 22 is detected, net X-ray data P1 can be obtained even if scattered ray components SDM extending at the bottom of this X-ray intensity are removed. However, when this X-ray intensity is as indicated by the solid line in FIG. 22, the amount of (the degree of contribution of) scattered rays is large relative to net X-ray data P2. Therefore, if the scattered ray components SDM are removed in this state, the net X-ray data P2 becomes almost "0", and this makes it difficult, or impossible, to obtain the value of the data. This scattered ray correction process can eliminate such "abuses".

As described above, whether to perform the scattered ray correction process, or the amount of intensity of scattered ray components to be actually subtracted, is determined by using the above-mentioned parameter. This determination is preferably performed such that the degree of contribution of scattered ray components with respect to the whole X-ray data detected is about 5 to 10%.

In the above description, whether to perform the scattered ray correction process is determined on the basis of the beam thickness "or" the patient size. However, the present invention is not limited to this form. For example, it is also possible to regard the beam thickness and the patient size as having an organic relationship. In this case, no scattered ray correction process is performed as long as both the beam thickness and the patient size are equal to or smaller than first and second predetermined values (these values have the nature of a watershed which determines whether to perform the scattered ray correction process). That is, in this processing, the scattered ray correction process is performed if the patient size is larger than the second predetermined value although the beam thickness is equal to or smaller than the first predetermined value.

In short, the present invention can determine whether to perform the scattered ray correction process, or to determine the amount of intensity of scattered ray components to be actually subtracted, in accordance with the combination of the beam thickness and the patient size.

Additional advantages and modifications will readily occur to those skilled in the art. Therefore, the invention in its broader aspects is not limited to the specific details and representative embodiments shown and described herein. Accordingly, various modifications may be made without departing from the spirit and scope of the general inventive concept as defined by the appended claims and their equivalents.

What is claimed is:

1. An X-ray CT scanner for reconstructing a CT image of a subject, comprising:
an X-ray source configured to emit an X-ray beam;
an X-ray detector having a plurality of detecting elements and configured to detect X-rays transmitted through the subject;
a reconstructing unit configured to reconstruct the CT image based on an output of the X-ray detector;
a determining unit configured to allow a user to set a thickness of the X-ray beam to an arbitrary integral multiple of a pitch of the detecting elements, as measured in a body axis direction of the subject, by graphically manipulating a frame representing the ends of the X-ray beam;
a control unit configured to generate a calibration data file used to correct projection data obtained using the set X-ray beam thickness, from stored calibration data corresponding to predetermined X-ray beam thicknesses other than the set X-ray beam thickness; and
a display unit configured to display a scanogram based on the reconstructed CT image, and to graphically display on the scanogram, the frame representing the ends of the X-ray beam set by the determining unit.

2. The scanner according to claim 1, wherein the display unit is configured to display, on the scanogram, information regarding a scanning range covered by a helical scan.

3. The scanner according to claim 1, wherein the display unit is configured to display a cursor indicating a center of an X-ray beam and a cursor indicating ends of an X-ray beam.

4. The X-ray CT scanner of claim 1, wherein the control unit is configured to generate the calibration data file by interpolation using the stored calibration data and the set X-ray beam thickness.

5. The X-ray CT scanner of claim 1, wherein the control unit is configured to generate the calibration data file by extrapolation using the stored calibration data and the set X-ray beam thickness.

6. An X-ray CT scanner, comprising:
an X-ray tube configured to emit X-rays;
an X-ray detector having a plurality of detecting elements and configured to detect X-rays transmitted through a subject;
a scanogram generating unit configured to generate scanogram data based on an output of the X-ray detector;
an image reconstructing unit configured to reconstruct tomographic data based on an output of the X-ray detector;
a display unit;
a screen generating unit configured to generate data of an X-ray beam thickness setting support screen, which is to be displayed on the display unit, the X-ray beam thickness setting support screen including the scanogram and a frame including both ends of an X-ray beam obtained in accordance with a thickness of the X-ray beam arranged on the scanogram;
a manipulating unit configured to allow a user to graphically manipulate a size of the frame so as to set the thickness of the X-ray beam to an arbitrary integral multiple of a pitch of the detecting elements; and
a control unit configured to generate a calibration data file used to correct projection data obtained using the set X-ray beam thickness, from stored calibration data corresponding to predetermined X-ray beam thicknesses other than the set X-ray beam thickness.

7. The X-ray CT scanner of claim 6, wherein the display unit is configured to display, on the scanogram, information regarding a scanning range covered by a helical scan.

8. The X-ray CT scanner of claim 6, wherein the display unit is configured to display a cursor indicating a center of an X-ray beam and a cursor indicating ends of an X-ray beam.

* * * * *